(12) United States Patent
Stanton

(10) Patent No.: US 10,004,585 B2
(45) Date of Patent: *Jun. 26, 2018

(54) GLUTEAL IMPLANTS AND IMPLANT SYSTEMS

(71) Applicant: Ryan A. Stanton, M.D., Inc., Beverly Hills, CA (US)

(72) Inventor: Ryan A. Stanton, Beverly Hills, CA (US)

(73) Assignee: Ryan A. Stanton, M.D., Inc., Beverly Hills, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/479,749

(22) Filed: Apr. 5, 2017

(65) Prior Publication Data

US 2017/0202653 A1 Jul. 20, 2017

Related U.S. Application Data

(63) Continuation of application No. 15/011,083, filed on Jan. 29, 2016, now Pat. No. 9,615,906.
(Continued)

(51) Int. Cl.
*A61F 2/12* (2006.01)
*A61F 2/00* (2006.01)

(52) U.S. Cl.
CPC .... *A61F 2/0059* (2013.01); *A61F 2220/0033* (2013.01); *A61F 2230/0008* (2013.01);
(Continued)

(58) Field of Classification Search
CPC ........ A61F 2/12; A61L 27/18; A61L 2430/04; C08L 83/04
See application file for complete search history.

(56) References Cited

U.S. PATENT DOCUMENTS

| 4,597,763 A | 7/1986 | Schweikhart |
| 5,026,394 A | 6/1991 | Baker |

(Continued)

FOREIGN PATENT DOCUMENTS

| MX | 2005002006 | 8/2006 |
| WO | WO 2015/021807 | 2/2015 |

OTHER PUBLICATIONS

International Search Report and Written Opinion in PCT App. No. PCT/US2016/015787 dated Apr. 28, 2016 in 8 pages.

*Primary Examiner* — Thomas J Sweet
*Assistant Examiner* — Tiffany Shipmon
(74) *Attorney, Agent, or Firm* — Knobbe, Martens, Olson & Bear, LLP

(57) ABSTRACT

Gluteal implants and gluteal implant systems are described herein, as are methods of manufacturing and implanting the same. In certain embodiments, the gluteal implant includes a body having a convex upper surface, a concave lower surface, and an edge, the edge being formed by the intersection between the convex upper surface and the concave lower surface. The body can take on various shapes, including a truncated ovoid shape, a truncated approximate ovoid shape, a truncated substantially ovoid shape, a truncated ellipsoid shape, a truncated approximate ellipsoid shape, or a truncated substantially ellipsoid shape, among others. In certain embodiments, the gluteal implant system includes first and second gluteal implants that have the same or different shaped bodies. In certain embodiments, the gluteal implants and gluteal implant systems are implanted in a buttock region.

21 Claims, 26 Drawing Sheets

Related U.S. Application Data

(60) Provisional application No. 62/192,993, filed on Jul. 15, 2015, provisional application No. 62/109,557, filed on Jan. 29, 2015.

(52) U.S. Cl.
CPC .......... *A61F 2230/0093* (2013.01); *A61F 2250/0062* (2013.01)

(56) References Cited

U.S. PATENT DOCUMENTS

| | | |
|---|---|---|
| 5,662,708 A | 9/1997 | Hayes et al. |
| 7,081,135 B2 | 7/2006 | Smith et al. |
| 8,480,735 B2 | 7/2013 | Rigotti et al. |
| 8,708,955 B2 | 4/2014 | Tilson et al. |
| 8,808,373 B2 | 8/2014 | Boyden et al. |
| 9,615,906 B2 | 4/2017 | Stanton |
| 2004/0143327 A1 | 7/2004 | Ku |
| 2007/0276485 A1 | 11/2007 | Paganon |
| 2010/0023130 A1 | 1/2010 | Henry et al. |
| 2011/0264213 A1 | 10/2011 | DeMiranda |
| 2012/0259428 A1 | 10/2012 | Brogan et al. |
| 2012/0330427 A1 | 12/2012 | Yaremchuk |

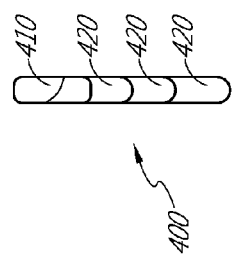
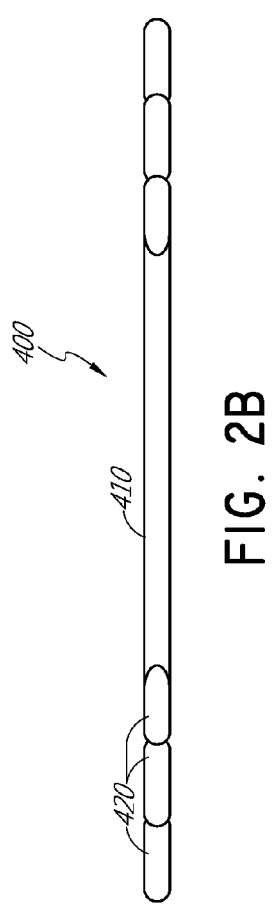
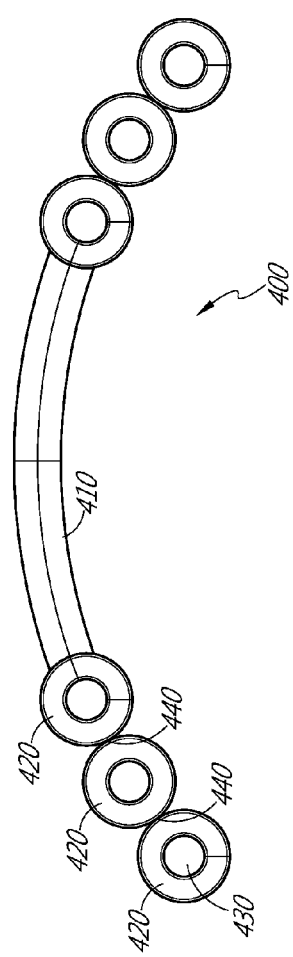

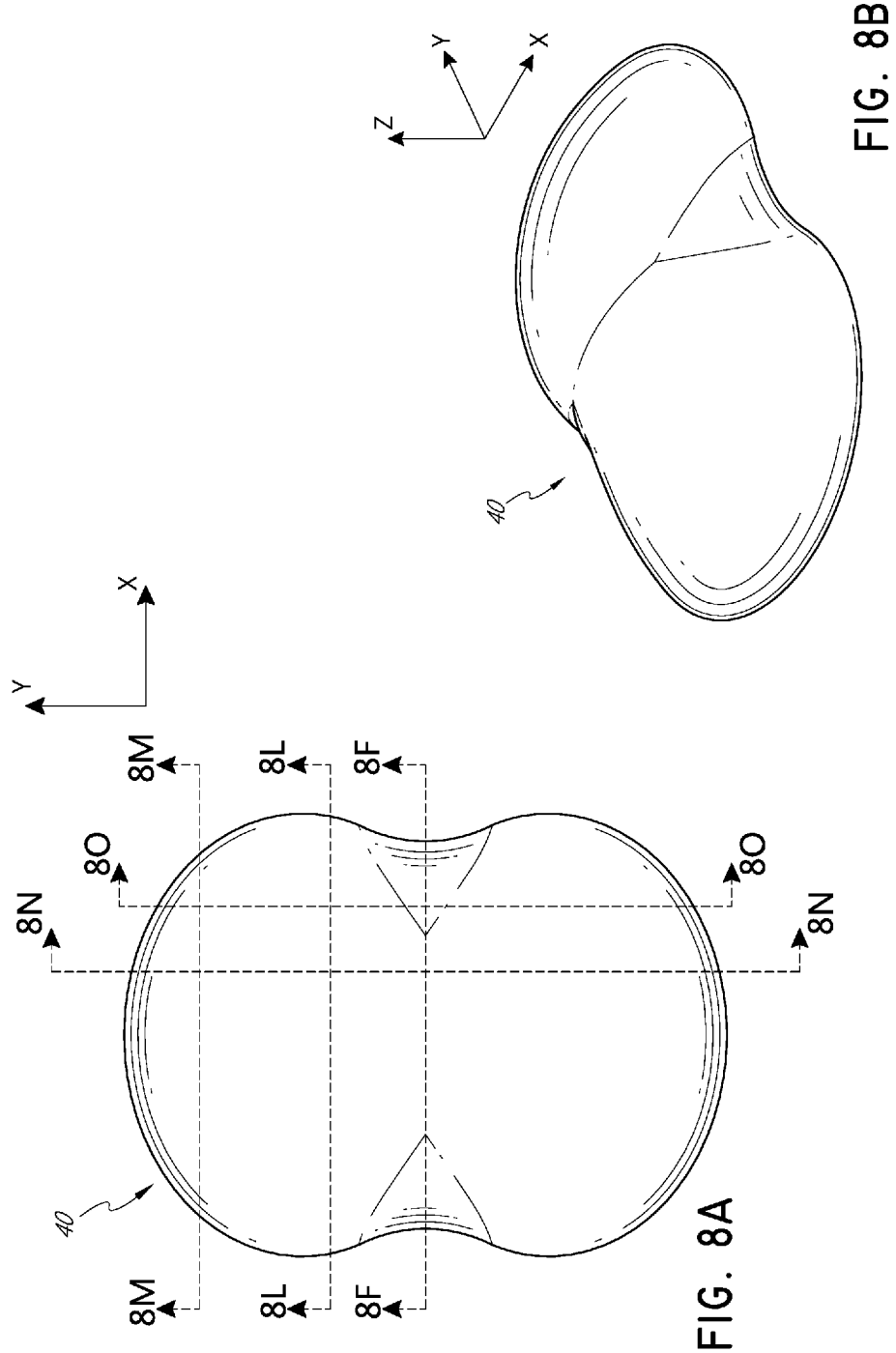

GLUTEAL IMPLANTS AND IMPLANT SYSTEMS

CROSS-REFERENCE TO RELATED APPLICATIONS

This application claims the benefit under 35 U.S.C. § 120 as a continuation of U.S. patent application Ser. No. 15/011,083 filed on Jan. 29, 2016, which in turn is a nonprovisional application of 35 U.S.C. § 119(e) of U.S. Provisional Application Nos. 62/109,557, filed Jan. 29, 2015, and 62/192,993, filed Jul. 15, 2015, both titled "GLUTEAL IMPLANT SYSTEM FOR PREVENTION OF MALROTATION." The disclosure of each of these prior applications is hereby incorporated by reference in their entireties herein.

BACKGROUND

Field of the Disclosure

The present disclosure relates generally to implants for augmenting or reconstructing the human body. In particular, the present disclosure relates to gluteal implants, as well as to gluteal implant systems.

Description of the Related Art

Implants may be used to augment and/or reconstruct the human body. However, current implants are unstable and prone to shifting after implantation, which can cause a host of problems for both patients and doctors alike. For example, among other problems, post-operative shifts can (1) cause patients pain, discomfort, and embarrassment, (2) necessitate additional doctor intervention (e.g., invasive or noninvasive), and/or (3) prolong patient recovery times. Accordingly, a need exists not only for implants and implant systems that prevent, inhibit, conceal, and/or mitigate post-operative shifts that move implants and implant systems out of position, but also for implants and implant systems that alternatively or additionally encourage and/or facilitate restorative shifts that move implants and implant systems back into position during and/or following any post-operative shift that moves them out of position.

SUMMARY OF SOME EMBODIMENTS

The implants, implant systems, and methods described herein each have several aspects, no single one of which is solely responsible for its desirable attributes. Without limiting the scope of this disclosure as expressed by the claims which follow, some features are described briefly below. After considering this description, and particularly after reading the section entitled "Detailed Description of Some Embodiments," one will understand the advantageous features of the implants, implant systems, and methods described herein.

In some embodiments, a gluteal implant can comprise a body comprising a convex upper surface, a concave lower surface, and a peripheral edge, the edge defined by the intersection between the convex upper surface and the concave lower surface. In some embodiments, the body is symmetrical across two orthogonal reference planes and can comprise one of a truncated ovoid shape, a truncated approximate ovoid shape, a truncated ellipsoid shape, and a truncated approximate ellipsoid shape. In some embodiments, the convex upper surface can comprise one of a portion of a first surface selected from the group consisting of an ovoid surface, an approximate ovoid surface, an ellipsoid surface, and an approximate ellipsoid surface, said first surface having a first semi-major axis and a first radius of curvature and a first semi-minor axis and a second radius of curvature. In some embodiments, the concave lower surface can comprise one of a portion of a second surface selected from the group consisting of an ovoid surface, an approximate ovoid surface, an ellipsoid surface, and an approximate ellipsoid surface, said second surface having a second semi-major axis and a third radius of curvature and a second semi-minor axis and a fourth radius of curvature. In some embodiments, the first radius of curvature differs from the third radius of curvature, wherein the difference is between about 2.22 cm and about 2.62 cm. In some embodiments, the second radius of curvature differs from the fourth radius of curvature, wherein the difference is between about 2.72 and about 3.12. In some embodiments, the convex upper surface and the concave lower surface intersect at an angle ranging from about 25 degrees to about 39 degrees. In some embodiments, the convex upper surface forms a peak of the implant. In some embodiments, the concave lower surface forms a peak of a concavity. In some embodiments, the edge forms a bottommost point of the implant. In some embodiments, the edge outlines an oval or ellipse when viewed from above.

In some embodiments, a gluteal implant system can comprise a first gluteal implant and a second gluteal implant. In some embodiments, the first and second gluteal implants can have convex curved superior first and concave second inferior surfaces, the curvature of the first surface being different from the curvature of the second surface. In some embodiments, the first and second gluteal implants can have reflective symmetry about exactly two orthogonal planes. In some embodiments, the first and second gluteal implants comprise a body having one of a truncated ovoid shape, a truncated approximate ovoid shape, a truncated ellipsoid shape, and a truncated approximate ellipsoid shape.

In some embodiments, a method of implanting a gluteal implant can comprise preparing a surgical site, forming a cavity in a buttock region, and implanting a gluteal implant disclosed herein.

Details of one or more embodiments of the subject matter described in this application are set forth in the accompanying drawings and the description below. Any of the features, components, or details of any of the arrangements or embodiments disclosed in this application are combinable and modifiable to form myriad new arrangements and embodiments that fall within the spirit and scope of this disclosure. Other features, aspects, and advantages will also become apparent from the description, the drawings, and the claims. Note that the relative dimensions of the following figures may not be drawn to scale.

BRIEF DESCRIPTION OF THE DRAWINGS

Embodiments will now be described with reference to the following drawings, which are provided by way of example, and not by way of limitation. Like reference numerals indicate identical or functionally similar elements.

FIGS. 2A-2C are various views of the restraining connector of FIG. 1.

DETAILED DESCRIPTION OF SOME EMBODIMENTS

Figure 1A:
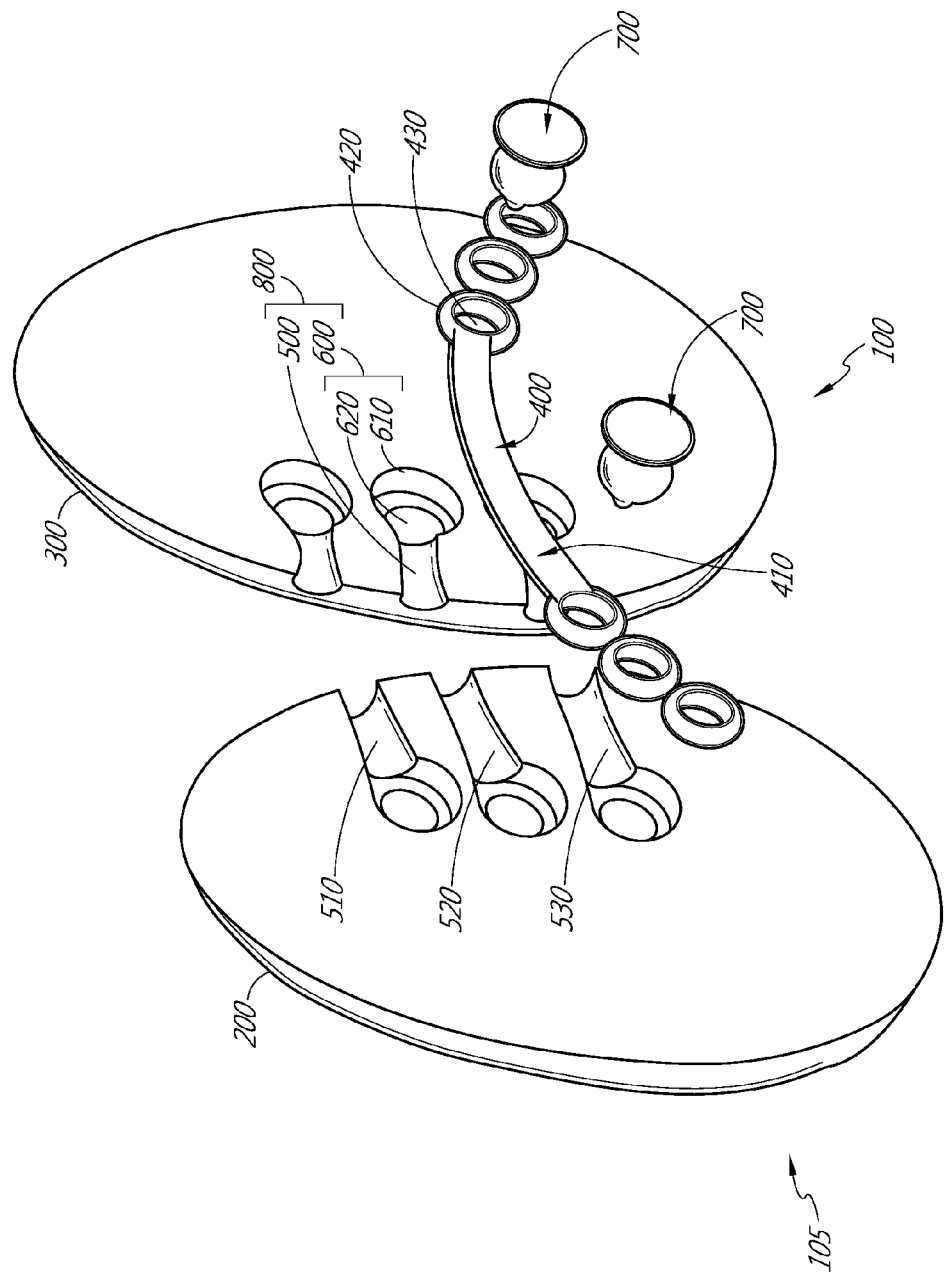
FIGS. 1A-1C are various perspective views of an implant stabilizing system.

Embodiments of the present disclosure provide implants and implant systems for human bodies. In particular, the present disclosure relates to implants and implant systems which prevent, inhibit, conceal, and/or mitigate post-operative shifts (also referred to as post-operative movement) that move implants and implant systems out of position, as well as to implants and implant systems that alternatively or additionally encourage and/or facilitate restorative shifts that move implants and implant systems back into position during and/or following any post-operative shift that moves them out of position. For example, in some aspects, implants and implant systems are described which prevent, inhibit, conceal, and/or mitigate post-operative mal-rotation and/or mal-translation events, and in some aspects, implants and implant systems are described which alternatively or additionally encourage and/or facilitate restorative movements which bring implants and implant systems back into position during and/or following post-operative mal-rotation and/or mal-translation events.

In some aspects, implants that are restrained relative to one another are described, and in some aspects, implants that are unrestrained relative to one another are described. Specifically, in certain embodiments, implants and implant systems are described which include stabilizing features that link two or more implants together and/or that anchor one or more of the implants to the surrounding tissue, and in certain embodiments, implants and implant systems are described which do not include stabilizing features that link two or more implants together and/or that do not include stabilizing features that anchor one or more of the implants to the surrounding tissue. Further, in certain embodiments, implants and implant systems are described which are configured to positionally self-correct back into position, facilitatively and/or automatically, when moved out of position (e.g., automatically translate and/or rotate back into position after having been moved out of position). While certain embodiments are described below, these embodiments are presented by way of example only, and can be embodied in myriad ways.

Implants are generally described as being one of two main shapes: non-round (e.g., teardrop, ovoid, spheroid, oval, ellipse or disk), which are asymmetrical except about one or two planes or axes of symmetry, and round (e.g., circle, sphere, or hemisphere), which are symmetrical about an infinite number of planes or axes. However, it should be appreciated that many non-round conventional implants that are described with modifiers that connote reflective symmetry across two planes of symmetry actually do not have any plane of symmetry (e.g., "ovoid," "ellipsoid," and "teardrop") because rather than describing the three-dimensional shape of the implant, such modifiers are often used to describe the two-dimensional shape of the implant's projected perimeter onto a frontal plane when viewed from above. It should also be appreciated that ovals, ellipses, and circles are two-dimensional shapes and that ovoids, ellipsoids, spheres, and spheroids are three-dimensional shapes.

Non-round and round implant shapes function similarly in some cases but produce different aesthetic results and carry different degrees of post-operative movement risk. Aesthetically, non-round implants can in some cases create more naturally appearing anatomical curves than round implants. However, with respect to risk, non-round implants have a greater chance than round implants of post-operatively shifting out of position. Thus, while non-round implants can advantageously provide patients with a higher level of aesthetic satisfaction, they can also lead to more post-operative complications since they are less stable.

The higher risk of post-operative movement that is associated with non-round implants can be a product of myriad factors, including: (1) non-round implants having too much symmetry (e.g., ovoid implants are symmetrical about three planes of symmetry) and (2) conventional non-round implants are unrestrained relative to one another. As a result of either of these factors, ovoid buttock implants, for example, have been said to carry a greater chance of post-operatively mal-translating and at least a 50% or more incidence of post-operatively mal-rotating (mal-translating and mal-rotating are also separately and/or collectively referred to as shifting and post-operative movement). As used herein, mal-translation is the undesired gradual or sudden translation (e.g., straight and/or curved planar movement) of an implanted implant, and mal-rotation is the undesired gradual or sudden rotation (e.g., clockwise or counterclockwise movement relative to a frontal plane) of an implanted implant. It should be appreciated that mal-translation and mal-rotation can occur separately or together.

When an implant mal-translates and/or mal-rotates, it can cause patients a number of problems, including pain, discomfort, and a change in physical appearance, among others. For example, anatomically incorrect or unpleasing aesthetics can form in the buttock region as a result of post-operative shifts. Since implants are not designed to move back into position following a post-operative shift, doctors typically need to perform some sort of corrective action to bring the implant back into position.

The corrective action used will depend on the severity of the post-operative shift, such as, for example, whether it is mild, moderate, or severe, among others. Generally, such action may include prescribing additional pain medication for mild post-operative movement, manually manipulating (e.g., de-rotating and/or de-translating) the implant for moderate post-operative movement, or surgically adjusting (e.g., de-rotating and/or de-translating) the implant for severe post-operative movement. However, manual manipulation and surgical correction can not only cause the patient to experience additional pain and discomfort on top of the pain and discomfort already caused by the implant shifting out of position, such methods can also prolong the patient's recovery time by additionally traumatizing the implant region. Patients may also develop secondary medical conditions that need to be treated, which can complicate the recovery process even more. For example, mal-translation and/or mal-rotation events can cause patients to feel unhappy about their body image to the extent that their mental health is put in jeopardy (e.g., depression, anxiety, etc.), and until the post-operative shift is effectively managed or corrected, such secondary medical conditions might also need to be treated.

To summarize, post-operative movements can cause problems for doctors and patients alike. Specifically, post-operative movements can inconvenience patients by causing them unexpected discomfort, prolonged recovery times, and a host of secondary conditions. Similarly, post-operative movements can inconvenience doctors by causing them to devote additional time, money, and resources to correct implantations that were properly implanted to begin with. Further, post-operative mal-translations and/or mal-rotations, as well as the problems associated therewith, may manifest at any time, both in the short and long term. Thus, while non-round implants can produce better aesthetic results than round implants, they nevertheless have a greater chance of causing the aforementioned problems than round implants since non-round implants have a higher chance of shifting out of position.

As a result, patients currently face a binary decision when choosing implants: either (1) choose an implant with better aesthetic properties, or (2) choose an implant with better stability. That is, while non-round implants may be more aesthetically pleasing, they nevertheless have a greater tendency to shift out of position relative to their round counterparts, and while round implants may be less aesthetically pleasing, they nevertheless have a lesser tendency to shift out of position relative to their non-round counterparts. Thus, a need exists for non-round implants that are more stable and/or for non-round implants that can more easily move back into position. Specifically, a need exists for implants and implant systems which prevent, inhibit, conceal, and/or mitigate post-operative shifts, as well as for implants and implant systems that alternatively or additionally encourage and/or facilitate restorative shifts that move implants and implant systems back into position during and/or following any post-operative shift that moves them out of position.

In certain embodiments, the instability associated with current implants is solved and/or improved by restraining one or more implants relative to one another and/or relative to one or more stabilizing features (e.g., a restraining connector). For example, in certain embodiments, two or more implants (e.g., ellipsoid, sphere, or spheroid implants having ellipse shaped perimeter projections onto a frontal plane) are restrained relative to one another by connecting at least two of them together with one or more stabilizing features, and in certain embodiments, each implant is alternatively or additionally restrained relative to itself with one or more stabilizing features (e.g., restraining connectors and/or tissue anchors). In certain embodiments, one or more of these connections and/or stabilizing features are configured to stabilize implants in a way that prevents, inhibits, conceals, and/or mitigates post-operative shifts. As a result, many of the post-operative movement complications associated with non-round implants can be reduced or eliminated, thereby saving both patients and doctors from the inconveniences and problems discussed above.

Turning to FIG. 1A, FIG. 1A illustrates an implant mal-rotation and/or mal-translation stabilizing system 100, such as, for example, a gluteal implant stabilizing system. As illustrated in FIG. 1A, the stabilizing system 100 comprises multiple components intended to be assembled together. For example, in the illustrated embodiment, the stabilizing system comprises a plurality of implants 105 configured for a left and right buttock, at least one restraining connector 400 configured for secure attachment to the plurality of implants 105, and a plurality of restraining fasteners 700 to secure the at least one restraining connector 400 to the plurality of implants 105. In certain embodiments, the stabilizing systems described herein (e.g., stabilizing system 100) allow a first implant to be tethered (also referred to as linked, coupled, attached, leashed, etc.) to a second implant and/or to the human body. For example, in certain embodiments, the stabilizing system 100 links two or more implants together such that each of the two or more implants is physically coupled to one or more other implants.

In certain embodiments, the plurality of implants 105 comprises a right gluteal implant 200 and a left gluteal implant 300 configured to receive a portion of one or more restraining connectors 400 and one or more restraining fasteners 700. However, it should be appreciated that left and right breast implants are also appreciated, as well as implants for any other anatomical location. It should also be appreciated that the plurality of implants 105 can comprise any suitable number of implants, such as, for example, one, two, three, four, or more implants, among others.

In certain embodiments, the restraining connector 400 can include an adjustable or fixed central elongate member 410 (similar to a leash structure) with one, two, or more removable lateral rings 420 attached to or proximate each terminal end. In certain embodiments, the stabilizing system 100 can include more or less components. For example, in certain embodiments, the stabilizing system 100 is manufactured as a unitary system by, for example, a molding or co-molding process. As another example, in certain embodiments, the stabilizing system 100 can include two or more restraining connectors 400. However, any suitable number of components and features which restrain two or more implants together is appreciated.

As further shown in FIG. 1A, a surface of each of the plurality of implants 105 comprises one or more surface features, such as depressions 800 configured for receiving one or more restraining connectors 400 and one or more restraining fasteners 700. The surface depressions 800 can include one or more medial restraining grooves 500 and one or more associated pairs of medial apertures 600. The restraining grooves 500 are configured to receive a portion of the central elongate restraining member 410 and the apertures 600 are designed to accommodate a lateral ring 420 and a restraining fastener 700. In certain embodiments, the plurality of restraining grooves 500 each terminate with at least one terminal aperture 600, wherein each aperture 600 further comprises a surface cavity 610 and an interior cavity 620. In some embodiments, the surface cavity 610 can have a diameter that is larger than that of the interior cavity 620. The surface cavity 610 is configured to receive a lateral ring 420 and also house a portion of a restraining fastener 700. The interior cavity 620 is configured to receive a portion of a restraining fastener 700. Other aperture designs and housing accommodations are also appreciated, for example, in some embodiments, the cavities and rings need not necessarily be circular in shape, and can be square, triangular, oval, or any other suitable shape. Moreover, in some embodiments, it is appreciated that the surface features need not necessarily be part of a shell of the implant per se, but are part of a housing/casing sized and configured to hold an implant within a cavity of the housing, akin to a pillowcase.

FIG. 1A also illustrates that the restraining connector 400 is configured to connect the plurality of implants 105. The restraining connector 400 is sized and shaped so that a restraining groove 500 and a cavity 600 or a pair of complementary cavities 600 can receive it. To secure the restraining connector 400 to an implant, restraining fasteners 700 are used to anchor (also referred to as fasten) the restraining connector 400 to one or more cavities 600 on each of the plurality of implants 105. Anchoring is accomplished by pushing, or otherwise moving a fastener 700 through a fastener hole 430 of a lateral ring 420 into an aperture 600 on one or more of the plurality of implants 105. Other anchoring mechanisms such as snap-fit components, threaded screws, zip ties, and the like can also be utilized, and for which the surface features of the implant (e.g., depressions 800) can be adapted to accommodate. Such anchoring mechanisms can be designed to prevent the restraining connector from detaching from an implant post-operation.

The restraining connector 400 secures the plurality of implants 105 relative to one another, which can reduce or prevent post-operative mal-rotation and/or mal-translation of the plurality of implants 105. This is because the restraining connector restrains and/or resists unwanted motion, and in some cases can be configured to exert tension on the implants 105. As discussed above, post-operative implant movement can occur during the healing process or at any time post-recovery. Such movement can include mal-translation, mal-rotation, or some combination thereof. Without a restraining connector 400, such post-operative shifting is opposed only by the internal resistive forces exerted by the human body against each implant at and/or proximal the respective implant site. Thus, depending on the magnitude of the countervailing forces subjecting the implant to translation and/or rotation, such translation or rotation may be minimally opposed if a restraining connector (e.g., restraining connector 400) is not utilized to tether the plurality of implants together. By contrast, restraining connectors (e.g., restraining connector 400) link implants together to create a combined implant that has a larger size, shape, and mass that better resists post-operative translational and/or rotational movement of one or more of the tethered implants. That is, with the restraining connector, post-operative movement is reduced or eliminated because the plurality of implants 105 can no longer move independently without also communicating some fraction of that movement to one or more of the other implants and to one or more other parts of the human body. In this way, mal-rotational and/or mal-translational forces experienced by an implant are resisted by another implant and the surrounding tissue structure and vice versa. Further, in certain embodiments, the stabilizing system 100 can be implanted such that the restraining connector applies a post-operative force (e.g., a preload) on the plurality of implants designed to counteract post-operative movement, such as, for example, typical rotation events. For example, in certain embodiments, the restraining connector is optionally configured and implanted to apply a post-operative tension and/or compression between and/or among one or more implants in any suitable direction(s). In such embodiments, the restraining connector may likewise reduce and/or eliminate post-operative movement.

The implant stabilizing system 100 illustrated in FIG. 1A is also optionally adjustable. For example, in certain embodiments, the stabilizing system 100 is adjustable in a variety of directions, such as, for example, within a plane defined by two orthogonal reference axes. In some embodiments, the one, two, or more restraining grooves 500 are generally oriented in a medial-lateral direction and spaced apart in a superior-inferior direction, although it should be appreciated that the grooves can also and/or instead be oriented and/or spaced apart in any suitable fashion, such as, for example, diagonally. In certain embodiments, the restraining grooves 500 can comprise a first top groove 510, a second middle groove 520, and a third bottom groove 530, as well as associated apertures 600. In certain embodiments, one, two, three, or more apertures 600 are associated with each groove on each implant surface. However, it should be appreciated that any suitable number of grooves and any suitable number of apertures are envisioned. For example, in some embodiments, one or more grooves without an aperture are utilized. It should also be appreciated that different grooves can have different relative orientations and different numbers of apertures associated therewith. For example, in some embodiments, the implant surface includes more or less than three grooves, and in some embodiments, each groove terminates with more or less than three associated apertures, such as, for example, one, two, four, five, or more grooves, and/or one, two, four, five, or more associated apertures. To illustrate, just as the restraining connector has one or more lateral rings 420 at each terminal end, the one or more restraining grooves 500 may likewise have one or more apertures 600 at their corresponding terminal ends. Advantageously, a plurality of restraining grooves and apertures on the implant provides a physician with multiple site options and multiple anchor points for the restraining connector, thereby better enabling the doctor to optimize both the positioning and anchoring of the implant stabilizing system. As shown in FIG. 1A, the multiple restraining grooves and apertures allow a doctor to customize the implant stabilizing system 100 according to each patient's physiological needs and/or personal desires.

In modifying the implant stabilizing system 100 for a particular patient, a doctor can make adjustments to the restraining connector 400 itself. For example, in some embodiments, the central elongate member 410 is non-adjustable and terminates at each end with one or more removable lateral rings 420 and fastener holes 430. By removing one or more lateral rings 420, the length of the restraining connector 400, and therefore the distance (also referred to as a gap) between the plurality of implants 105, can be adjusted. Removal can be accomplished by cutting or snapping the ring from the connector or via some other removal method. In some embodiments, the lateral rings 420 not utilized for fastening do not need to be removed, and thus can be preserved for post-operative adjustment if necessary. In other embodiments, the central elongate member 410 is an adjustable member that can lock into place. For example, the central elongate member 410 can be extendible, compressible, rotatable, or any suitable combination thereof. These adjustments similarly allow the gap between the plurality of implants 105 to be modified. In addition, the rotational aspect of the central elongate member 410 also allows the plurality of implants 105 to sit in different planes from one another, which may or may not be necessary depending on patient physiology. It should be appreciated that the adjustable segment of the central elongate member 410 can include any portion thereof and can be realized in any suitable fashion. In some embodiments, the central elongate member can include one or more removable lateral rings 420 as well as an adjustable central elongate member 410 that can lock into place. In some embodiments, the central elongate member 410 can include one or more lockable hinges to adjust the angle between the plurality of implants 105.

Having the capability to adjust the implant stabilizing system 100 can be important since it can make it easier to accommodate the physical and mental health needs of more people. For example, depending on the patient, myriad factors and/or events may combine to cause or create physical imperfections and/or mental health issues. For example, a patient may have undergone severe trauma to the implant region, a patient may have experienced excessive gluteal weight gain through poor diet and exercise habits, a person may have been the victim of uncontrollable outside stressors which lead to excessive weight loss and a resulting decrease in buttock mass, a patient may have been born with a congenital buttock defect, a patient may have had a mastectomy, a patient may have received an unrestrained implant system which later rotated or translated out of position, or a patient might be unhappy with their body image.

As described above, and as shown in FIG. 1A, the plurality of implants 105, the restraining connector 400, and the one or more restraining fasteners may be separate components, and can be composed of any suitable biocompatible material such as silicone and/or plastic, among others. In certain embodiments, the stabilizing system 100 is manufactured from, for example, silicone or silicone reinforced with a material such as Dacron. However, other materials and combinations are also envisioned. For example, in some embodiments, the connector 400 and the restraining fasteners 700 are combined into a single element. Further, in some embodiments, the implant shape is round or non-round (e.g., oval), or any other customizable shape that facilitates buttock augmentation and/or reconstruction, including implant geometries described elsewhere herein. For example, in FIG. 1A, the implants are ovoid shaped. In some embodiments the plurality of implants 105 have different shapes relative to one another, and in some embodiments, they are the same shape relative to one another.

Figure 1B:
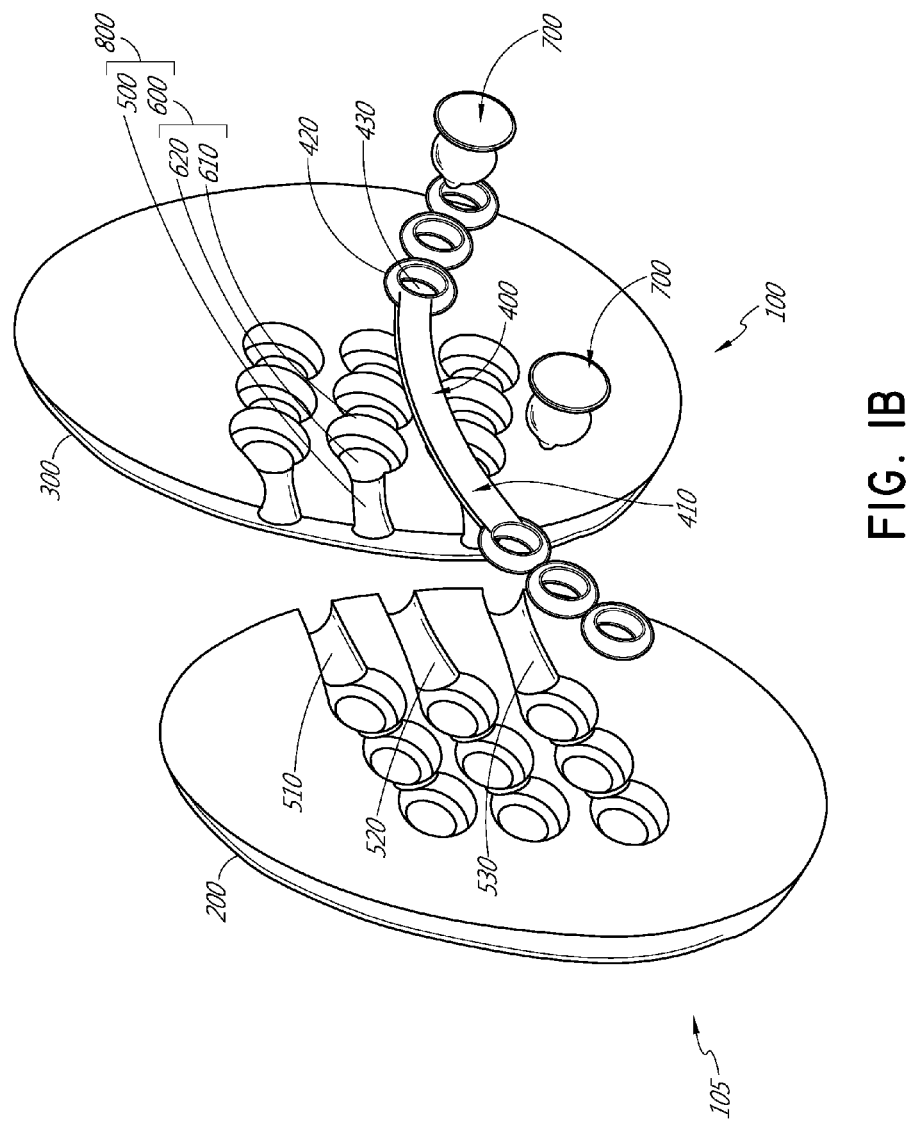
Figure 1C:
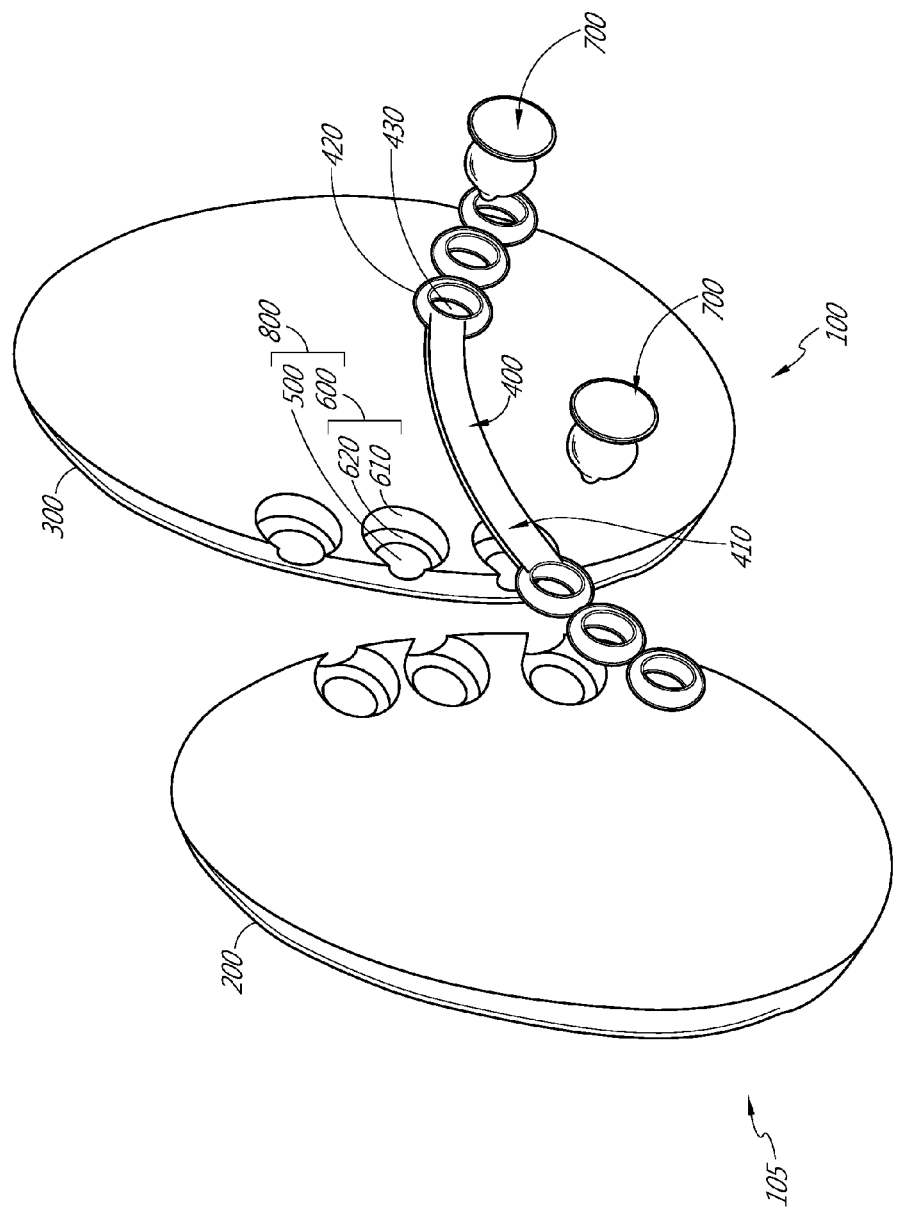

FIGS. 1B and 1C illustrate variations of the embodiment depicted in FIG. 1A. For example, FIG. 1B illustrates an implant restraining system 100 having a plurality of apertures 600 positioned adjacent one another. For example, FIG. 1B illustrates three apertures adjacently positioned such that one, two, or three rings 420 can be inserted into the implant to adjust the width between the implants 200, 300. In certain embodiments, the width between the implants 200, 300 can be adjusted by removing one or more rings 420 from the restraining connector 400 and positioning the restraining connector in the desired surface depressions. In certain embodiments, no rings are removed prior to implantation. FIG. 1C illustrates an implant restraining system 100 without the grooves 510, 520, 530. In such embodiments, the width between the implants 200, 300 can be adjusted by removing one or more rings 420 from the restraining connector 400 and positioning the restraining connector in the desired surface depressions. In certain embodiments, no rings are removed prior to implantation.

FIGS. 2A-2C illustrate various views of the restraining connector 400 of the implant stabilizing system 100 illustrated in FIG. 1A. Specifically, FIG. 2A illustrates a front view of the restraining connector 400, FIG. 2B illustrates a top view of the restraining connector 400, and FIG. 2C illustrates a side view of the restraining connector 400. As discussed above, the restraining connector 400 is designed to link two or more implants together. This link is part of what reduces or prevents post-operative movement. As shown in FIG. 2A, the central elongate member 410, which is optionally fixed or adjustable, has one or more lateral rings 420 at each end. A fastener hole 430 is located through the center of each lateral ring 420. In addition, each ring, other than the two lateral rings 430 that are adjacent to the central elongate member 410, can be removed at their corresponding separation points 440. In some embodiments, the restraining connector 400 does not have any lateral rings 430 and is instead only an elongate bar with a straight and/or curved form that can be snapped or pushed into place. As further illustrated in FIG. 2A, the restraining connector 400 has a shape that mirrors the shape and orientation of the surface depressions 800 shown in FIG. 1A. In this case, the restraining connector 400 outlines an arc of an imaginary circle, but other shapes and orientations are also possible (e.g., straight or zig-zagged).

Figure 3A:
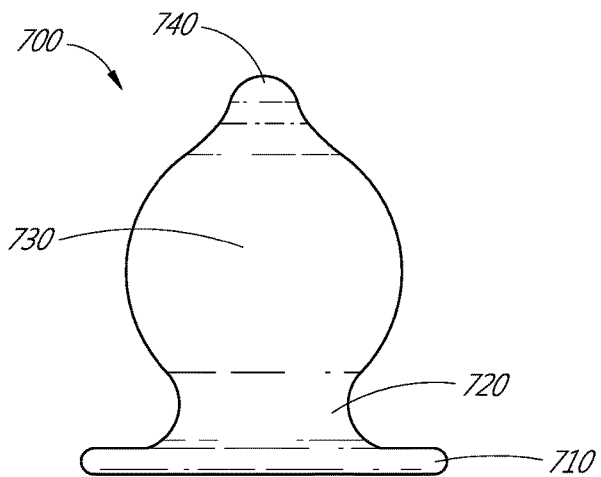
FIGS. 3A-3C are various views of the restraining fastener of FIG. 1.
Figure 3B:
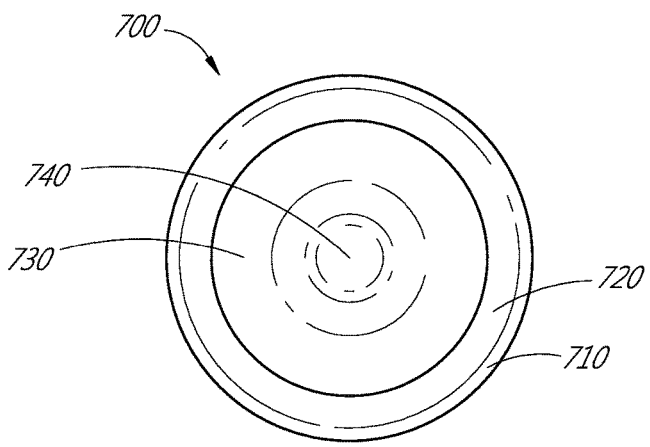
Figure 3C:
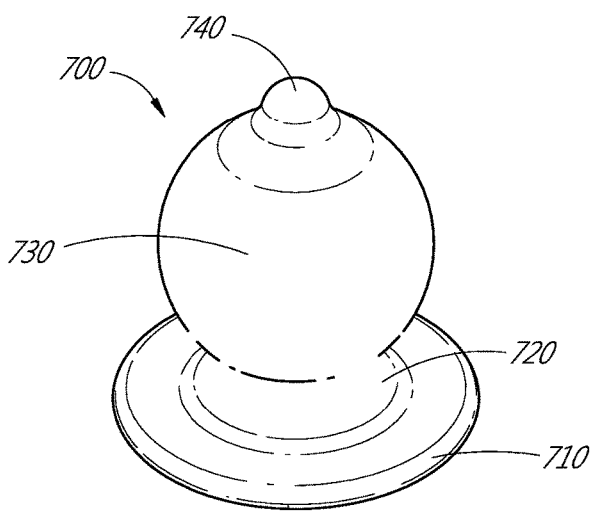

FIGS. 3A-3C illustrate various views of the restraining fastener 700 of FIG. 1A. Specifically, FIG. 3A illustrates a front view of the restraining fastener 700, FIG. 3B illustrates a top view of the restraining fastener 700, and FIG. 3C illustrates a perspective view of the restraining fastener 700. As shown in FIG. 3A, the restraining fastener 700 has a fastener top 710, a fastener ring 720, a fastener center 730, and a fastener tip 740. The fastener 700 is configured to secure one or more restraining connectors to a plurality of implants (see also FIGS. 1-2). Accordingly, the fastener 700 has a shape that fits through a lateral ring hole 430 and into an aperture 600 shown in FIG. 1A. In some embodiments, the fastener tip 740 and fastener center 730 fit into an interior cavity 620 by passing through a lateral ring hole that is positioned in a surface cavity 610. In some embodiments, the fastener tip 740 and fastener center 730 are first pushed through a lateral ring hole and then later pushed into an aperture 600. Once the fastener tip and center are through the ring, the fastener may "snap" into place, wherein the fastener ring 730 occupies the lateral ring hole in the surface cavity 610 and the fastener top covers the lateral ring 420 and ring hole 430 in or above the surface cavity 610. To pass through the lateral ring hole, the fastener should be made out of a material that is deformable but firm. For example, in some embodiments, the fastener is made from silicone reinforced with Dacron, however, any suitable material is appreciated. The fastener 700 can secure the restraining connector 400 to the implant such that the restraining connector does not become detached from any groove or aperture post-operation. The elongate member 410 can be either elastic or nonelastic in some embodiments. In some embodiments, the elongate member 410 can include one or more adjustment mechanisms, such as a spool, ratchet, or the like to adjust the distance between the first implant and the second implant postoperatively without necessarily requiring detachment of the elongate member 410 from the first implant and/or the second implant.

In certain embodiments, restrained and/or unrestrained implant systems can be used to help solve the problem of post-operative implant movement. In both types of systems, the implants can be any shape and have any surface that is symmetrical about two planes (e.g., two orthogonal planes). Some examples of implant shapes with symmetry about across two planes include shapes that are ellipsoids, approximate ellipsoids, substantially ellipsoidal, ovoids, approximate ovoids, substantially ovoidal, spheres, approximate spheres, substantially spherical, spheroids, approximate spheroids, substantially spheroidal, teardropoids, approximate teardropoids, substantially teardropoidal, paraboloids, approximate paraboloids, substantially paraboloidal, polygonoids, approximate polygonoids, or substantially polygonoidal, and truncations thereof, among any other suitable shape having curved and/or angular surfaces, including shapes with parametric and/or non-parametric surfaces. For unrestrained implant systems, the implant can be sized and shaped to have rotational symmetry about a center axis. The symmetry of the implant functions to conceal, or otherwise mitigate, the effects of post-operative movement. For example, in some embodiments, the implant can conceal mal-rotation events that rotate the implant 180 degrees or approximately 180 degrees (e.g., clockwise or counterclockwise) because the implant still has same aesthetic appearance at the implant site after the 180 degree or approximate 180 degree rotation. This is in contrast to conventional implants, which are, for example, tear-drop shaped and cannot be rotated 180 degrees and still have the same aesthetic appearance at the implant site. The implant geometries as noted herein can refer to the unconstrained natural implant shape, and/or their shape when implanted in the body in some embodiments.

Figure 4B:
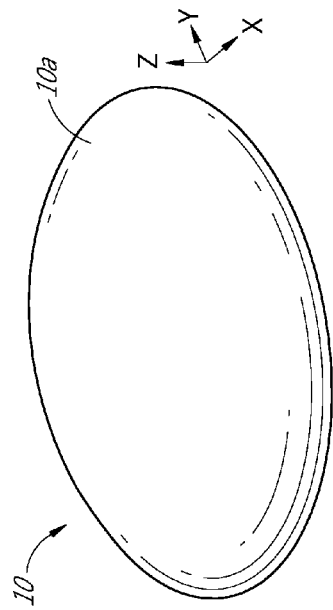
FIGS. 4A-4P are various views of a truncated approximately ovoid implant with a convex upper surface and a concave lower surface.
Figure 4C:
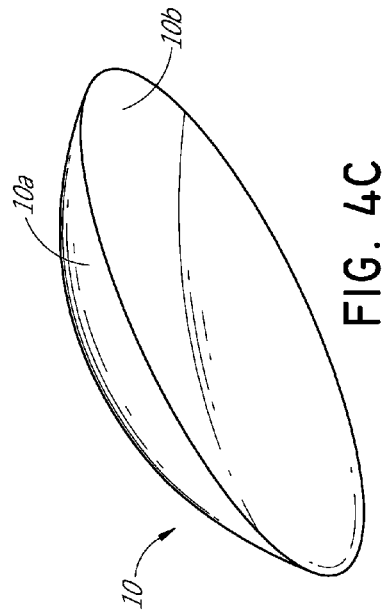
Figure 4A:
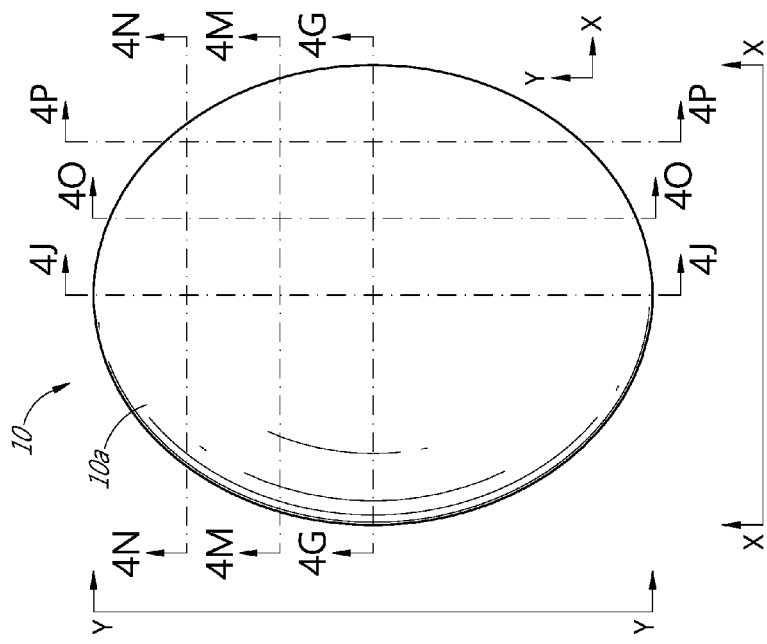
Figure 4F:
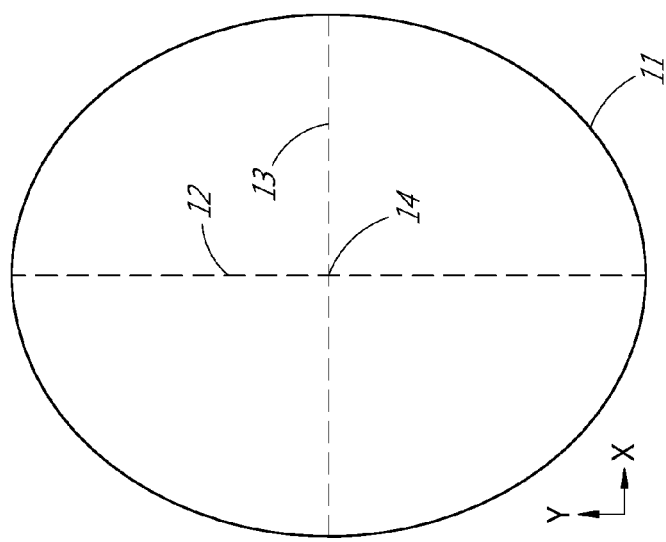
Figure 4D:
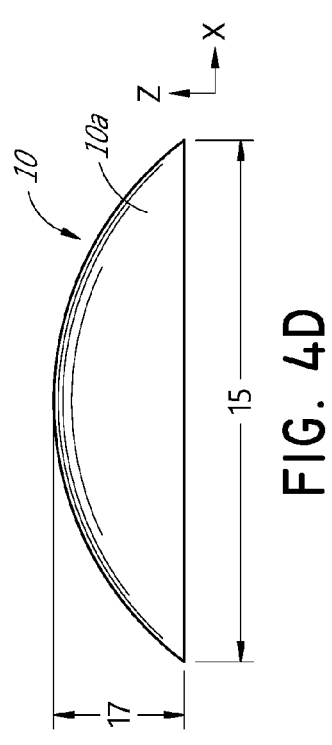
Figure 4E:
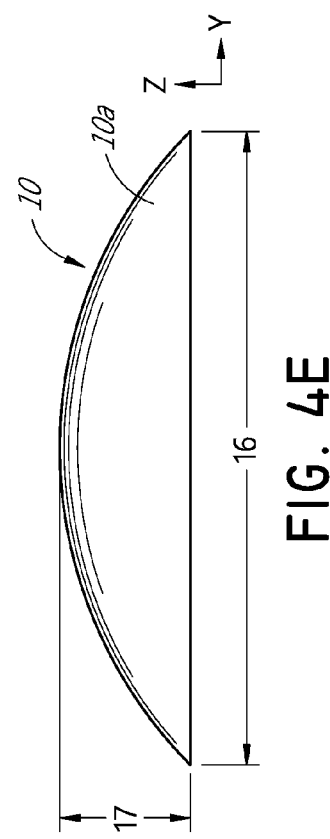
Figure 4G:
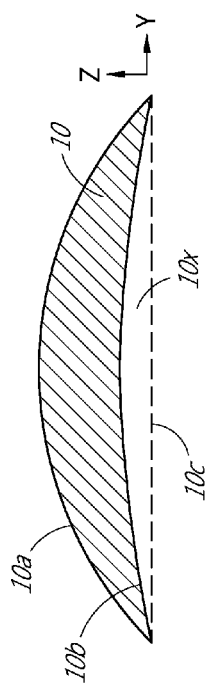
Figure 4J:
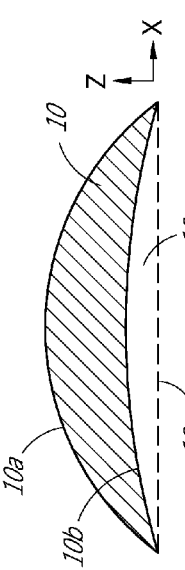
Figure 4H:
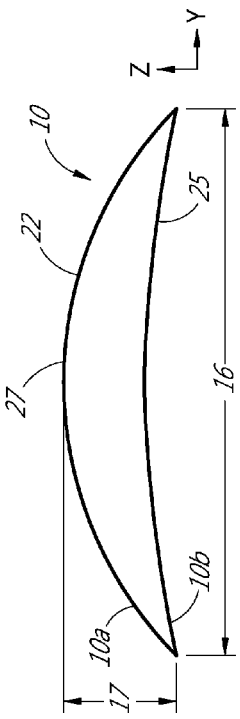
Figure 4K:
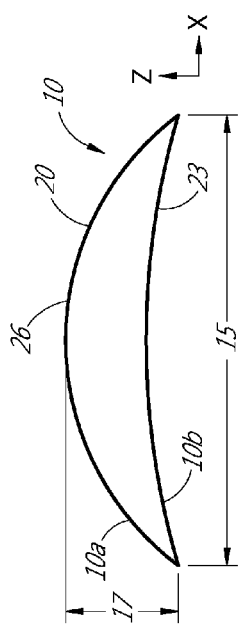
Figure 4I:
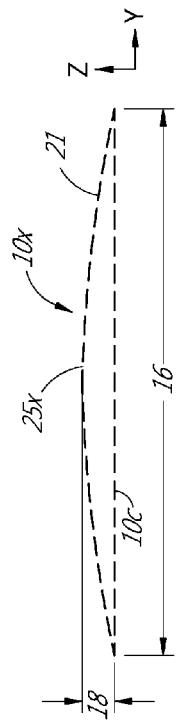
Figure 4L:
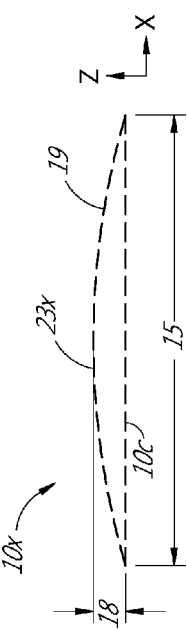
Figure 4M:
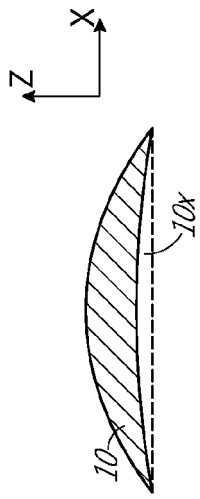
Figure 4N:
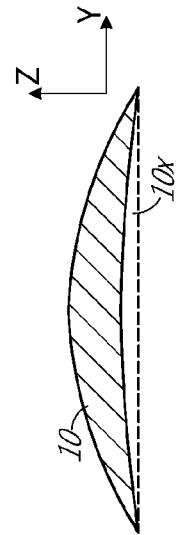
Figure 4O:
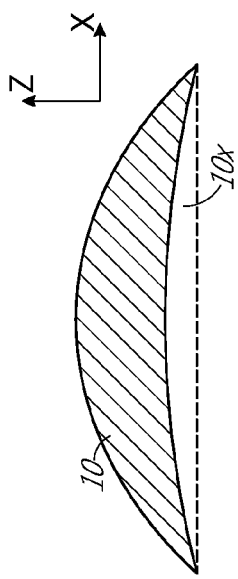
Figure 4P:
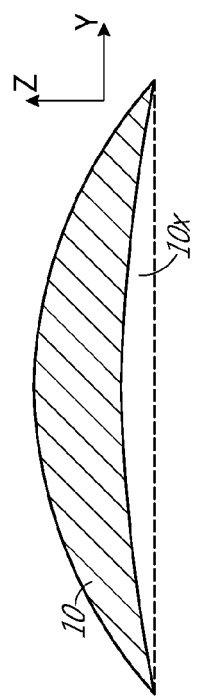
Figure 5B:
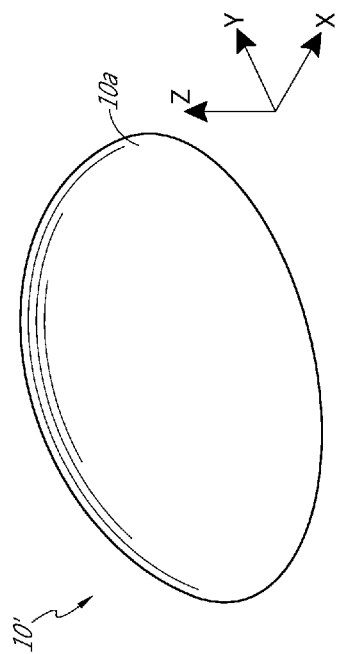
FIGS. 5A-5P are various views of a truncated ellipsoid implant with a convex upper surface and a concave lower surface.
Figure 5C:
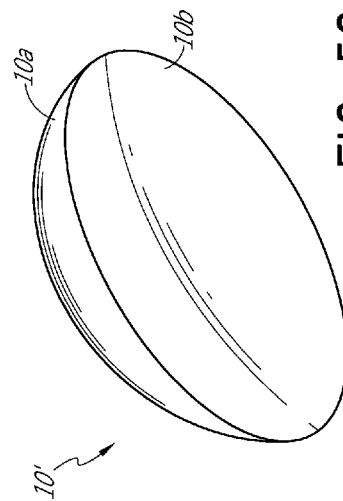
Figure 5A:
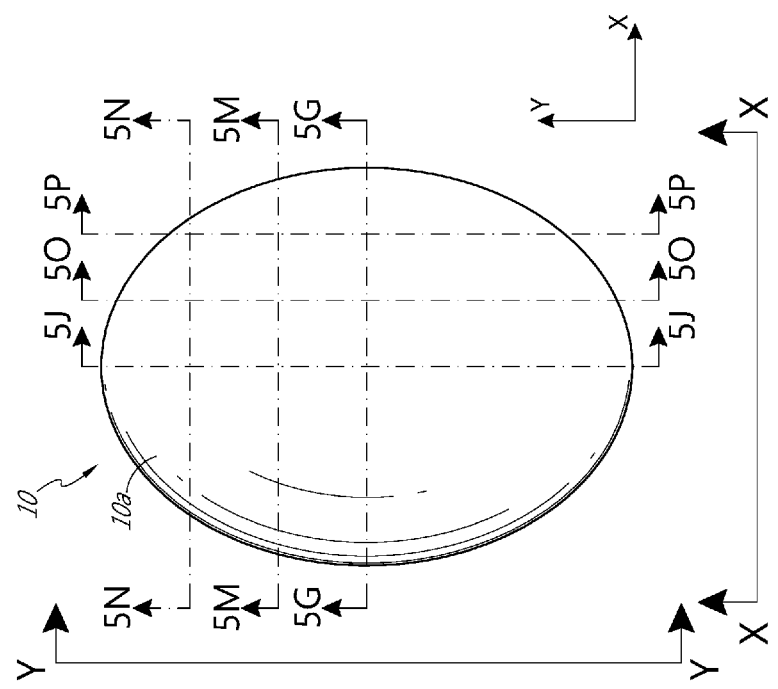
Figure 5F:
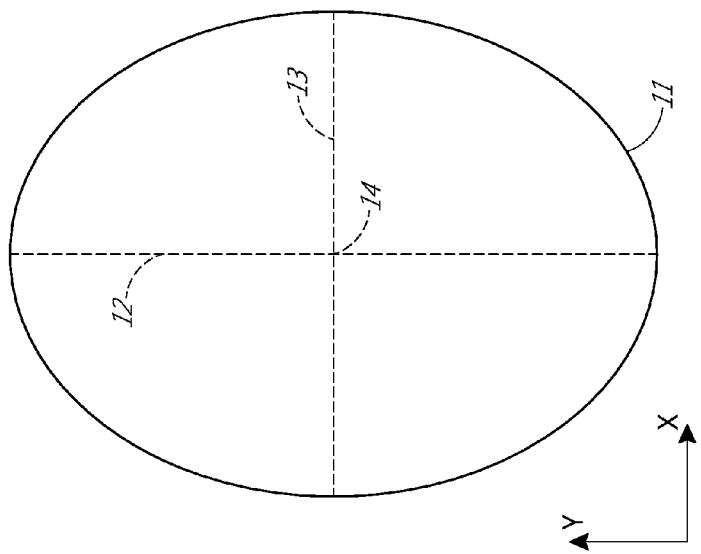
Figure 5D:
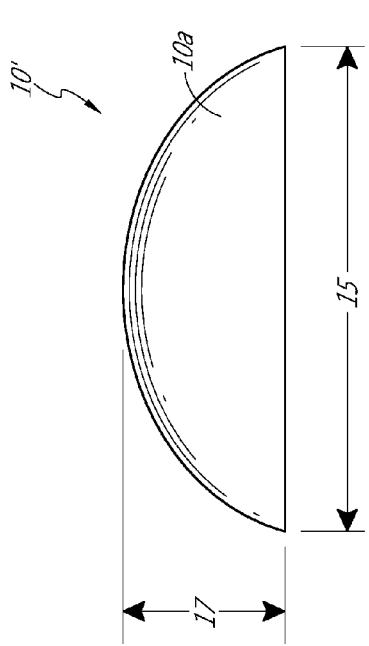
Figure 5E:
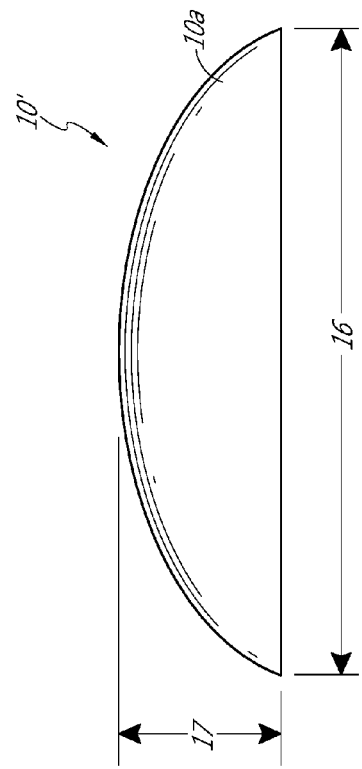
Figure 5G:
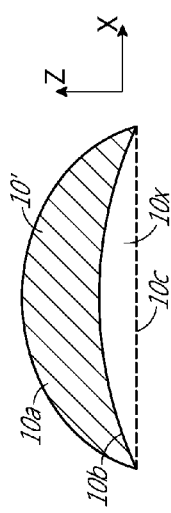
Figure 5J:
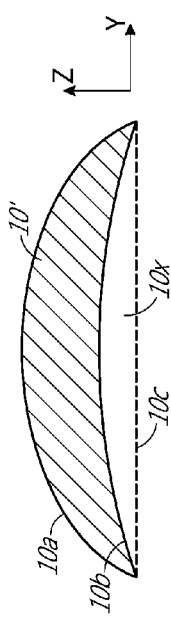
Figure 5H:
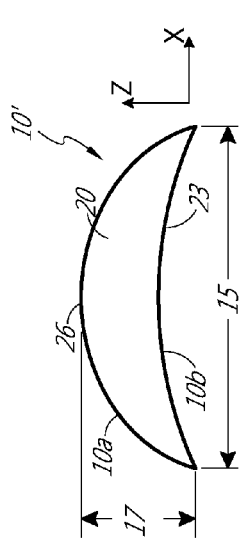
Figure 5K:
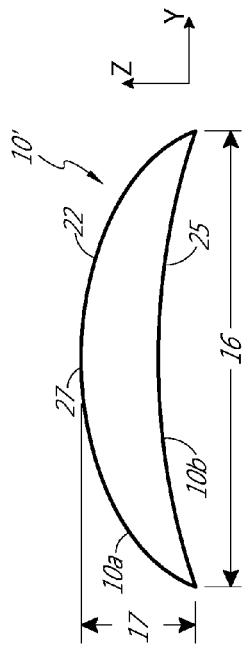
Figure 5I:
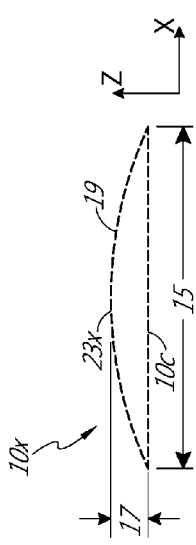
Figure 5L:
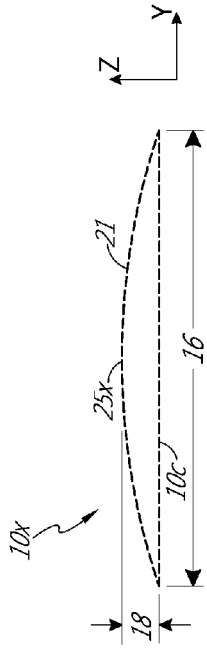
Figure 5M:
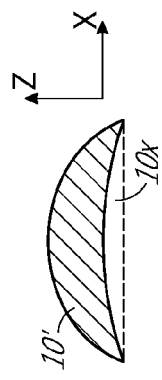
Figure 5N:
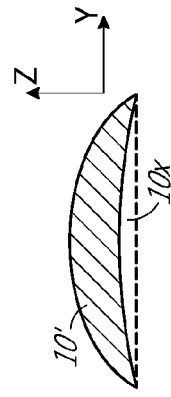
Figure 5O:
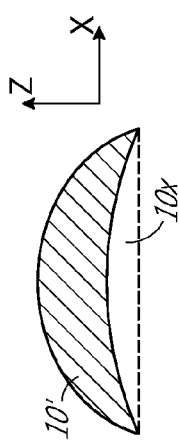
Figure 5P:
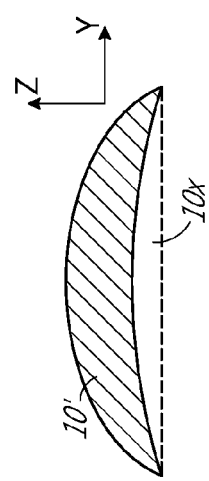

For example, FIGS. 4A-4P and 5A-5P illustrate various views of two implant shapes that have exactly two planes of reflective symmetry, and which are designed so that they can be rotated a desired amount, such as 180 degrees after implantation and not have the newly rotated position affect the aesthetics of the implant site. Specifically, FIGS. 4A-4P illustrate various views of an exemplary truncated approximately ovoid implant 10 with a convex upper surface and a concave lower surface, and FIGS. 5A-5P illustrate various views of an exemplary truncated ellipsoid implant 10' (also referred to as a truncated ovoid) with a convex upper surface and a concave lower surface. While not a perfect truncated ovoid in a strict geometrical sense, the implant 10 in FIGS. 4A-4P nevertheless closely resembles a truncated ovoid and is therefore referred to as a truncated approximately ovoid implant. In certain embodiments, the implants shown and described herein are formed from a section of one or more three dimensional bodies and/or surfaces. Like reference numerals between FIGS. 4A-4P and 5A-5P indicate the same or similar features having the same or similar properties. Thus, unless otherwise noted, reference numerals in FIGS. 5A-5P refer to features that are the same as or generally similar to the features of FIGS. 4A-4P (e.g., the implants 10, 10' have different surface curvatures).

With reference to FIGS. 4A-4P, the implant 10 can be used in any anatomical location, such as, for example, the chest, the face, the upper and lower extremities, and the buttocks, among others. As described above, the implant 10 can be configured to have rotational symmetry that conceals the effects of post-operative movement or suboptimal implantation technique, such as, for example, post-operative movement involving a 180 degree or approximately 180 degree shift about a center axis. These positions of rotational symmetry can correspond to positions of stability (also referred to as equilibrium positions). In certain embodiments, the implant can be sized and shaped so that it has two or more positions of stability, or only one position of stability. For example, the implant 10 can be configured to have a size and shape that is stable in one, two, or three equilibrium positions, among any other suitable number, the positions of stability being separated by any suitable angle, such as, for example, 180 degrees or approximately 180 degrees, 90 degrees or approximately 90 degrees, 45 degrees or approximately 45 degrees, among others. As used herein, equilibrium positions refer to anatomically natural, desired, and/or acceptable implant positions. In certain embodiments, the implant 10 is configured to resist/encourage movement away/toward the implant's equilibrium position(s).

In certain embodiments, the implant 10 is part of an implant system of two or more implants, such as, for example, a restrained or unrestrained implant system. For example, in certain embodiments, in addition to being adapted so that its size and shape helps stabilize it in one or more equilibrium positions, the implant 10 additionally includes and/or is coupled to one or more stabilizing features (e.g., a restraining connector and/or tissue anchor) as described above with reference to FIGS. 1-3C. However, in other embodiments, the implant 10 does not include a stabilizing feature and is not connected to another implant, but is instead stabilized with its size and shape alone, in addition to any interaction it has with the human body.

In certain embodiments, the implant 10 is configured to positionally self-correct back into an equilibrium position after having been moved out of that or a different equilibrium position, either facilitatively or automatically. For example, in certain embodiments, the implant 10 automatically translates and/or rotates back into an equilibrium position following a post-operative shift. Similarly, in certain embodiments, the implant 10 facilitates the manual translation and/or rotation of itself back into an equilibrium position. For example, in certain embodiments, an external source can "nudge" or apply a force of longer duration to the implant so that it moves back into an equilibrium position. In certain embodiments, the external source need only provide an initial nudge, after which the implant 10 auto-translates and/or auto-rotates back into a position of stability. In other embodiments, the external source can apply a continuous or varying force against the implant to manually translate and/or rotate it back into an equilibrium position, during which the implant 10 can facilitate such manual manipulation by being predisposed to return to a position of stability.

For example, in certain embodiments, after the implant 10 has been implanted, it is predisposed or otherwise inclined, at least partly because of its shape and/or size (1) to remain in its equilibrium position, (2) to resist any departure therefrom, and (3) to return to the same or to a different equilibrium position if a disruptive force causes a post-operative shift that moves it out of position. For example, as discussed above, the implant 10 is sized and shaped to encourage and/or facilitate restorative movements that bring the implant back into one of its equilibrium positions during and/or following a post-operative mal-rotation and/or mal-translation event. In such embodiments, when a post-operative shift occurs, the implant 10 is or can be subjected to restorative forces directed toward an equilibrium position that moves the implant 10 back into a position of stability.

The restorative forces can originate internally and/or externally relative to a person's body. For example, internal restoring forces can originate from surrounding tissue, from surrounding body structure, from the size and shape of the implant 10 itself, and/or from interactions between the implant 10 and the surrounding body (e.g., the implant cavity), and external restoring forces can originate from sources such as, for example, a person's hand, a chair, an electromagnetic force, or any suitable object or device. In certain embodiments, the internal restorative forces that develop in the implant region in response to post-operative shifts are alone sufficient to automatically move the implant 10 back into an equilibrium position, i.e., the implant 10 automatically self-corrects. In other embodiments, the internal restorative forces are aided by an external restorative force that together move the implant 10 back into an equilibrium position, i.e., the implant 10 facilitatively self-corrects in the sense that the size and shape of the implant makes it easier to return the implant 10 to an equilibrium position with outside help.

With reference to FIGS. 4A-4E, FIG. 4A illustrates a top elevational view, FIG. 4B illustrates a top perspective view, FIG. 4C illustrates a bottom perspective view, and FIGS. 4D and 4E illustrate two side elevational views of the implant 10. In particular, FIG. 4D is an elevational side view of the implant 10 in the XZ-plane viewed from the vantage point of line XX in FIG. 4A and FIG. 4E is an elevational side view in the YZ-plane viewed from the vantage point of line YY in FIG. 4A. As shown by lines XX and YY in FIG. 4A, the two side views illustrated in FIGS. 4D and 4E are orthogonal with respect to one another. Together, FIGS. 4A-4E illustrate that the implant 10 has exactly two reflective axes of symmetry about axes X and Y (or, equivalently, has exactly two planes of symmetry about reference planes YZ and XZ). However, it should be appreciated that reflective symmetry about any two (such as exactly two) suitable axes (or any two (such as exactly two) suitable reference planes) is envisioned, and that any suitable coordinate system can be used (e.g., spherical coordinates).

FIG. 4F illustrates a two dimensional projection of the perimeter of the implant 10 onto a frontal XY-plane from the perspective of FIG. 4A. Specifically, FIG. 4F illustrates that the outer profile 11 (also referred to as the perimeter or projection) of the implant 10 defines the shape of an oval or ellipse. However, other perimeter shapes are also appreciated, such as, for example, a circle. In certain embodiments, the profile 11 outlines the peripheral edge of the implant 10 where the concave lower surface intersects the convex upper surface. As shown in FIG. 4F, the outer profile 11 includes a major axis 12 (also referred to as the longer axis), a minor axis 13 (also referred to as the shorter axis), and a center 14. The major and minor axes 12, 13 are the longest and shortest diameters of the outer profile 11, respectively. The major and minor axes 12, 13 are mutually orthogonal and pass through the center 14. In certain embodiments, the minor axis 13 is coincident with the X axis and the major axis 12 is coincident with the Y axis, although any suitable axis arrangement is envisioned. In certain embodiments, the major and minor axes 12, 13 have lengths of 17 cm and 14 cm, respectively. In certain embodiments, the major axis is about 17 cm, such as between about 12 cm to about 22 cm, about 14 cm to about 20 cm, or about 15.5 cm to 18.5 cm, among any other suitable range. In certain embodiments, the minor axis is about 14 cm, such as between about 9 cm to about 19 cm, about 11 cm to about 17 cm, or about 12.5 cm to about 15.5 cm, among any other suitable range. Other major and minor axis lengths can include, for example, any suitable combination of major and minor axes having lengths in the range of 5 cm to 30 cm such that a mathematically defined ovular or elliptical perimeter and/or peripheral edge results. In certain embodiments, the major axis length is about 20% greater than the minor axis length, such as between about 10% and 30% greater, between about 12.5% and 27.5% greater, between about 15% and 25% greater, or between about 17.5% and 22.5% greater, among any other suitable range. Further, in certain embodiments, the major and minor axes 12, 13 each comprise an axis of symmetry.

Returning to FIGS. 4D and 4E, these figures also show that the implant 10 has a width 15, a length 16, and an outer height 17, as measured along axes X, Y, and Z. In certain embodiments, the width and length 15, 16 correspond to the minor and major axes 13, 12 shown in FIG. 4F. In certain embodiments, the width 15 is about 14 cm and the length 16 is about 17 cm, although any suitable dimension of the width and length is appreciated. For example, in certain embodiments, the width and length 15, 16 can have any dimension ranging from 5 cm to 30 cm which together cooperate to mathematically define an oval or ellipse. The outer height 17 is measured along the Z-axis between the lowermost point and topmost point of the implant 10. For example, for embodiments in which the lower surface of the implant is concave and the upper surface is convex, the outer height 17 represents the change in height along the Z-axis from the lowermost point to the topmost point of the implant as measured from its peripheral edge where the lower and upper surfaces converge (also referred to as its outer edge), to its topmost center where the upper surface is at its peak. In embodiments in which the lower surface of the implant is flat, the outer height 17 represents the change in height from any point on the lower surface of the implant to the topmost point of the implant where the upper surface is at its peak. In certain embodiments, the outer height 17 is about 3.5 centimeters, although any suitable outer height 17 is appreciated, such as, for example, between about 1 cm to about 15 cm, about 1 cm to about 10 cm, about 2 cm to about 8 cm, or about 2.5 to about 6.5 cm, among others. Moreover, in certain embodiments, the vertical distance (e.g., a dimension parallel to the Z axis along which the outer height 17 is measured) between the upper and lower surface in cross section does not taper to zero until the peripheral edge of the implant. For example, in some embodiments, the peripheral edge of the implant is formed by the intersection of the upper and lower surface such that the peripheral edge forms a point or substantially forms a point.

FIGS. 4G and 4J illustrate two cross-sectional side views of the implant 10, both of which cut through the center of the implant and split it in half. For example, the cross section shown in FIG. 4G illustrates the implant 10 in the XZ-plane at line 4G-4G in FIG. 4A, and the cross section shown in FIG. 4J illustrates the implant 10 in the YZ-plane at line 4J-4J in FIG. 4A. Similarly, FIG. 4M illustrates the implant 10 in the XZ-plane at line 4M-4M in FIG. 4A, FIG. 4N illustrates the implant 10 in the XZ-plane at line 4N-4N in FIG. 4A, FIG. 4O illustrates the implant 10 in the XZ-plane at line 4O-4O in FIG. 4A, and FIG. 4P illustrates the implant 10 in the XZ-plane at line 4P-4P in FIG. 4A. As shown in these figures, the arc lengths can decrease as the cross-sections are taken closer to the peripheral edge of the implant. For example, in certain embodiments, the shapes of the arcs approach one another until they merge into a single horizontal line at the peripheral edge of the implant. In certain embodiments, the distance between the upper and lower surfaces can decrease to zero toward the peripheral edge of the implant. In certain embodiments, the angle between the upper and lower surfaces can decrease to zero toward the peripheral edge of the implant. As shown in FIGS. 4A-4P, the slope of the surface of the implant varies.

For example, as shown in FIGS. 4G and 4J, as well as in FIGS. 4A-4P, the implant 10 has a convex upper surface 10a and a concave lower surface 10b, although it is appreciated that the upper and lower surfaces can be adapted to form any suitably shaped surface, such as, for example, flat, more curved, less curved, more convex, less convex, and/or angular, among others. The surfaces can be parametric and/or non-parametric surfaces. Although FIGS. 4G and 4J illustrate cross sections of the implant 10, it is appreciated that 10a, 10b are representative of surfaces, as labeled in FIGS. 4A-4P. In particular, FIGS. 4G and 4J illustrate the implant 10 with a convex upper surface 10a and a concave lower surface 10b and illustrate the concavity 10x with a convex upper surface 10b and a flat bottom surface 10c relative to the peripheral edge of the implant. It should be appreciated that the implant and concavity 10, 10x can take on any suitable size and any suitable shape relative to one another, as well as separately. For example, in certain embodiments, the concavity 10x can be defined relative to any reference surface below the lower surface 10b of the implant 10, such as, for example, a body cavity surface.

FIGS. 4H and 4I separately depict the cross-sectional side views of the implant and concavity 10, 10x illustrated together in FIG. 4G, and FIGS. 4K and 4L separately depict the cross-sectional side views of the implant and concavity 10, 10x illustrated together in FIG. 4J. In particular, FIG. 4H shows a profile 20 of the implant 10 in the XZ-plane, FIG. 4I shows a profile 19 of the concavity 10x in the XZ-plane, FIG. 4K shows a profile 22 of the implant 10 in the YZ-plane, and FIG. 4L shows a profile 21 of the concavity 10x in the YZ-plane. The concavity profiles 19, 21 illustrate a concavity height 18 (also referred to as an inner height of the implant) and the implant profiles 20, 22 illustrate the outer and inner heights 17, 18. The outer height 17 is determined as described above and the inner height 18 is similarly measured along the Z axis from a lowmost point along the perimeter of the concavity 10x to a topmost point of the concavity 10x. In certain embodiments, the inner height 18 is about 1 cm, such as between about 0.5 cm to about 1.5 cm, about 0.5 cm to about 2 cm, or about 1 cm to about 4 cm. Other inner heights are also appreciated, ranging from approximately 0.5 cm to approximately 0.5 cm less than the outer height 17, which can range from 1 cm to 15 cm, among any other suitable height.

The arcs 23x, 25x in FIGS. 4I and 4L correspond to the upper bounds of the concavity 10x in the cross-sectional profiles 19, 21. The inner arcs 23, 25 and the outer arcs 26, 27 in FIGS. 4H and 4K correspond to the concave lower and convex upper surfaces of the implant 10 in the cross-sectional profiles 20, 22. In certain embodiments, the arcs 23x, 23 are coincident or nearly coincident with each other and the arcs 25x, 25 are coincident or nearly coincident with each other. In certain embodiments, the inner arcs 23, 25 and the outer arcs 26, 27 in FIGS. 4H and 4K each correspond to a radius of curvature, such as, for example, approximately 25 cm for arc 23, approximately 18 cm for arc 25, approximately 9 cm for arc 26, and approximately 12 cm for arc 27. Other suitable radii of curvature are also appreciated, such as, for example, any suitable combination of radii ranging from about 5 cm to about 50 cm such that the inner arcs 23, 25 form part of the geometrical scaffolding of the concave surface of the implant 10 and such that the outer arcs 26, 27 form part of the geometrical scaffolding of the convex surface of the implant 10.

For example, in certain embodiments, the radius of curvature for the outer arc 26 is between about 7.5 cm to about 10.5 cm, about 6 cm to about 13 cm, or about 4.5 cm to about 14.5 cm., among any other suitable range. In certain embodiments, the radius of curvature for the inner arc 23 is between about 22.5 cm to about 27.5 cm, about 20 cm to about 30 cm, or about 17.5 cm to about 32.5 cm, among any other suitable range. In certain embodiments, the radius of curvature for the outer arc 27 is between about 10.5 cm to about 13.5 cm, about 9 cm to about 15 cm, or about 7.5 cm to about 16.5 cm, among any other suitable range. In certain embodiments, the radius of curvature for the inner arc 25 is between about 15.5 cm to about 20.5 cm, about 13 cm to about 23 cm, or about 10.5 cm to about 25.5 cm, among any other suitable range.

In some embodiments, the outer arc 26 has an arc length that is about 16.23 cm, such as between about 16.03 cm to about 16.43 cm, about 15.5 cm to about 17.0 cm, about 14 cm to about 18.5 cm, or about 11 cm to about 21.5 cm, among any other suitable range. In some embodiments, the inner arc 23 has an arc length that is about 14.20 cm, such as between about 14.00 cm to about 14.40 cm, about 12.5 cm to about 15.9 cm, about 10 cm to about 18 cm, or about 8.5 cm to about 23 cm, among any other suitable range. In some embodiments, the arc length of the outer arc 26 is about 15% greater than the arc length of the inner arc 23 in the XZ plane, such as between about 12% and 18% greater, between about 10% and 20% greater or between about 5% and about 30% greater. In some embodiments, the angle between the outer arc 26 and the inner arc 23 at the point at which they intersect at the peripheral edge of the implant is about 34 degrees, such as between about 33 degrees to about 35 degrees, about 30 degrees to about 38 degrees, about 20 degrees to about 38 degrees, about 15 degrees to about 40 degrees, or between about 10 degrees and 45 degrees, among any other suitable range.

In some embodiments, the outer arc 27 has an arc length that is about 18.85 cm, such as between about 18.65 cm to about 19.05 cm, about 17 cm to about 20.5 cm, about 15.5 cm to about 22 cm, or about 13 cm to about 24.5 cm, among any other suitable range. In some embodiments, the inner arc 25 has an arc length that is about 17.12 cm, such as between about 16.92 cm to about 17.32 cm, about 15.5 cm to about 19 cm, about 14 cm to about 20.5 cm, or about 12.5 cm to about 23 cm, among any other suitable range. In some embodiments, the arc length of the outer arc 27 is about 15% greater than the arc length of the inner arc 25 in the YZ plane, such as between about 12% and 18% greater, between about 10% and 20% greater or between about 5% and about 30% greater. In some embodiments, the angle between the outer arc 27 and the inner arc 25 at the point at which they intersect at the peripheral edge of the implant is about 29 degrees, such as between about 28 degrees to about 30 degrees, about 25 degrees to about 33 degrees, about 15 degrees to about 36 degrees, about 10 degrees to about 38 degrees, or between about 5 degrees and 40 degrees, among any other suitable range.

In certain embodiments, the ratio between the radius of curvature of the inner arcs 23, 25 can range from about 0.3 to about 1.7, such as, for example, approximately 0.4, 0.5, 0.6, 0.7, 0.8, 0.9, 1.0, 1.1, 1.2, 1.3, 1.4, 1.5, 1.6, or 1.7 or ranges incorporating any two of the preceding values. In certain embodiments, the ratio between the outer arcs 26, 27 can range from about 0.3 to about 3, such as, for example, approximately 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0, or ranges incorporating any two of the preceding values. In certain embodiments, the ratio between inner arc 23 and outer arc 26 can range from about 1.5 to about 6, such as, for example, approximately 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 4.0, 5.0, or 6.0, or ranges incorporating any two of the preceding values. In certain embodiments, the ratio between inner arc 25 and outer arc 27 can range from about 1.1 to about 3, such as, for example, approximately 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0, or ranges incorporating any two of the preceding values. Other suitable ratios are also appreciated. Such ratios advantageously make the implant 10 more aesthetically pleasing while also making it more stable in some embodiments. In some embodiments, any or all of the foregoing ratios are not 1.0.

In view of the aforementioned geometric parameters, and as described above, the implant 10 is not in some embodiments a truncated ovoid in a strict geometrical sense. Even so, the implant 10 is an illustration of a truncated approximately ovoid implant. This is because the implant 10 has the look and appearance of a truncated ovoid even though its geometric properties say otherwise. Thus, the implant 10 is described as a truncated approximately ovoid implant.

Figure 9A:
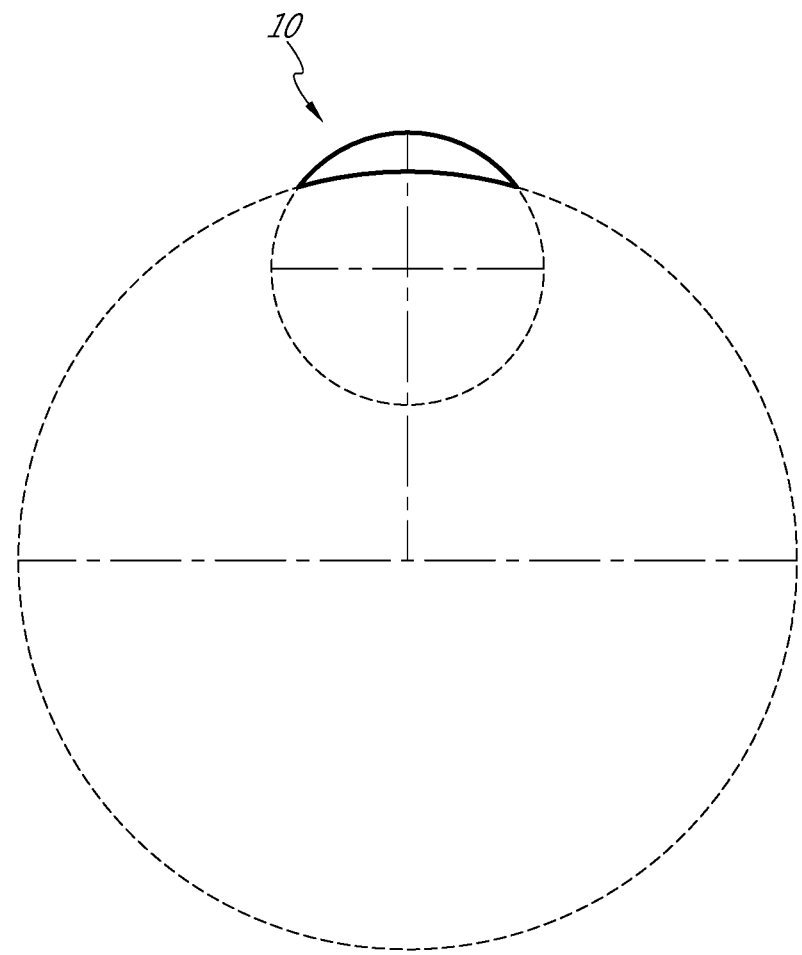
FIGS. 9A and 9B illustrate the cross-sections depicted in FIGS. 4H and 4K to further illustrate the type of two dimensional shape formed at the cross-section.
Figure 9B:
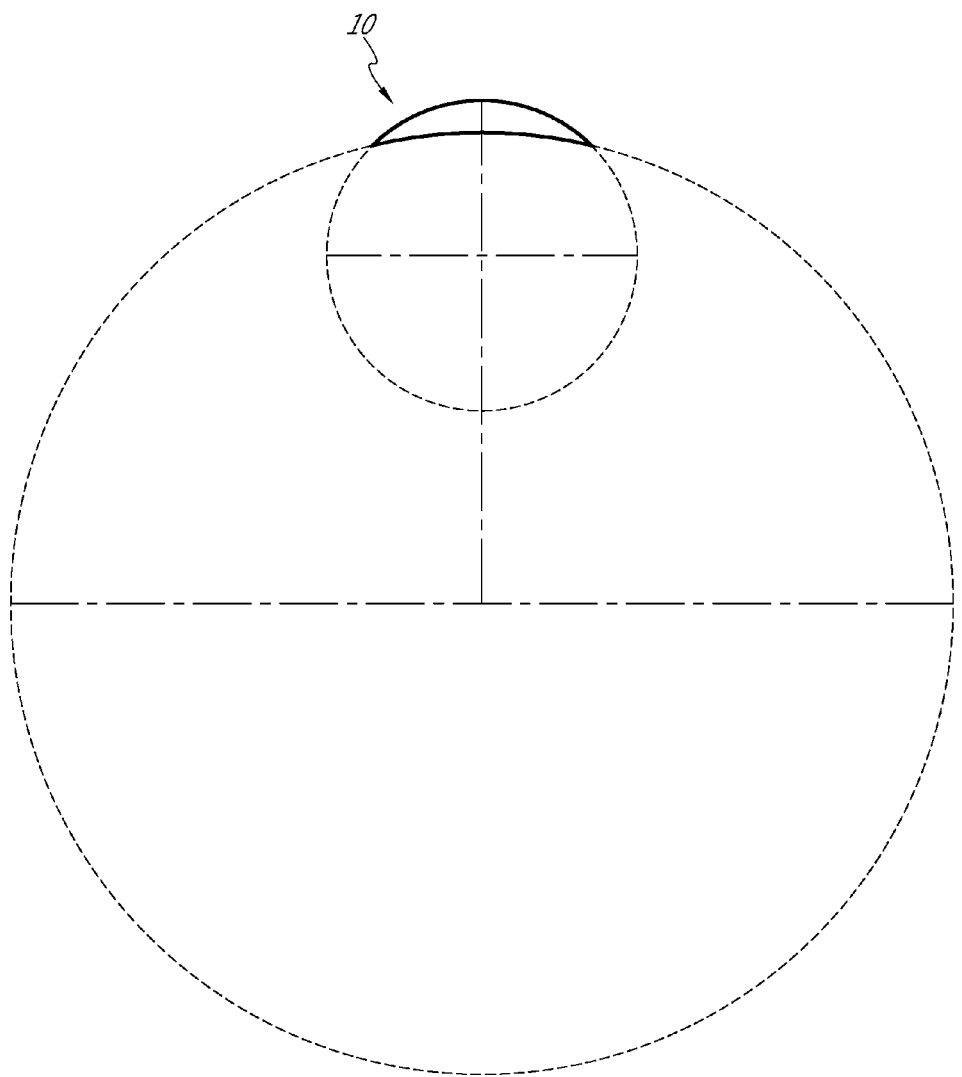
Figure 10A:
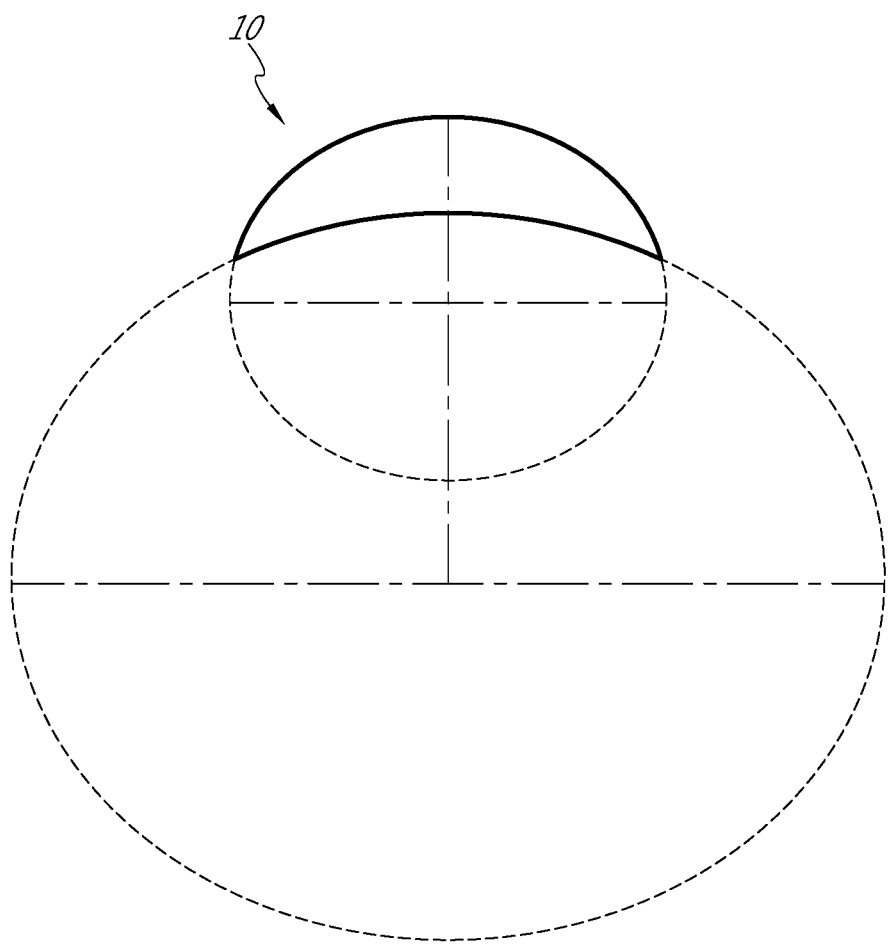
FIGS. 10A and 10B illustrate the cross-sections depicted in FIGS. 5H and 5K to further illustrate the type of two dimensional shape formed at the cross-section.
Figure 10B:
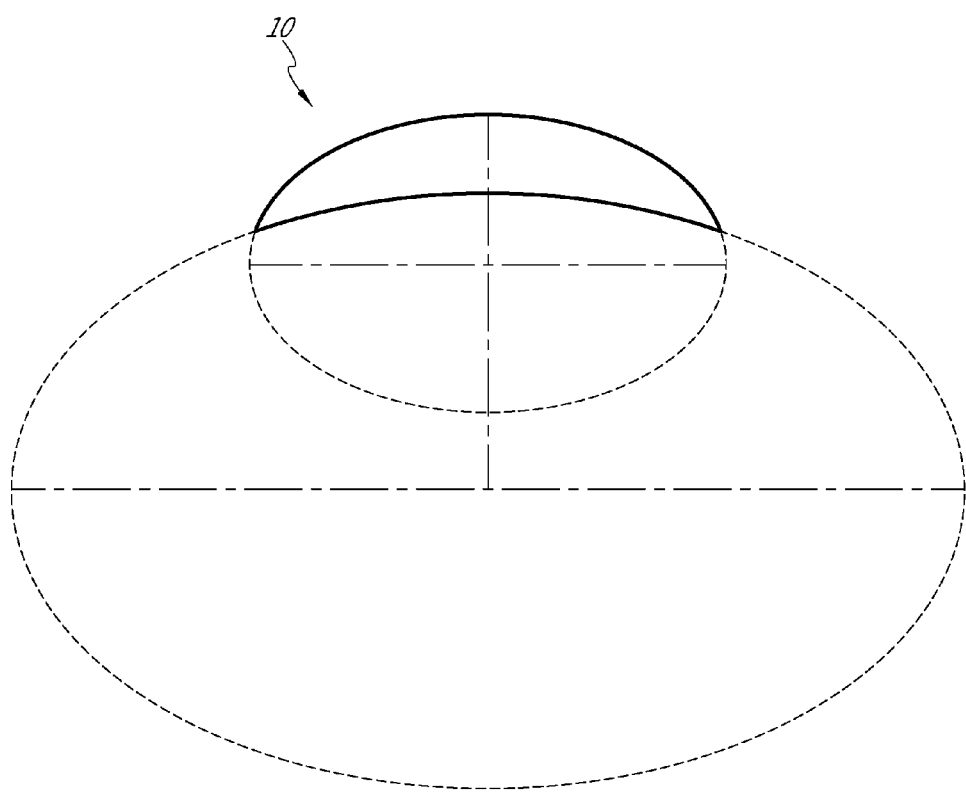

With reference to FIGS. 9A and 9B, these two figures illustrate the type of two dimensional shapes formed at the cross-sections depicted in FIGS. 4H and 4K. For example, FIG. 9A shows the relative curvature between the upper and lower surfaces shown in FIG. 4H, and FIG. 9B shows the relative curvature between the upper and lower surfaces shown in FIG. 4K. Similarly, FIGS. 10A and 10B illustrate two figures that show the two dimensional shapes that are formed at the center cross-sections depicted in FIGS. 5H and 5K. For example, FIG. 10A shows the relative curvature between the upper and lower surfaces shown in FIG. 5H, and FIG. 10B shows the relative curvature between the upper and lower surfaces shown in FIG. 5K.

With reference to FIGS. 5A-5P, in certain embodiments, the inner arcs 23, 25 and the outer arcs 26, 27 in FIGS. 5H and 5K have curvatures that vary according to an ellipse. For example, in certain embodiments, the inner arcs 23, 25 and the outer arcs 26, 27 in FIGS. 5H and 5K correspond to a semi-minor or semi-major axis of an ellipse. In certain embodiments, the arcs 23, 25, 26, 27 correspond to semi-minor/major axes ranging from about 7 cm to about 40 cm, such as, for example, approximately 24 cm for arc 23, 17 cm for arc 25, 10 cm for arc 26, and 13 cm for arc 27. Other suitable semi-minor and semi-major axes are also appreciated, such as, for example, any suitable combination of axes defining an ellipsoid ranging from about 5 cm to about 50 cm such that the inner arcs 23, 25 form part of the geometrical scaffolding of the concave surface of the implant 10' and such that the outer arcs 26, 27 form part of the geometrical scaffolding of the convex surface of the implant 10'.

In some embodiments, the inner arc of the upper surface and the inner arc of the lower surface are different, but within about 5% to about 10% of each other, within about 5% to about 20% of each other, within about 5% to about 40% of each other, or any other suitable percentage. In some embodiments, the outer arc of the lower surface and the outer arc of the upper surface are difference, but within about 5% to about 10% of each other, within about 5% to about 20% of each other, within about 5% to about 40% of each other of each other.

Again referencing FIGS. 4A-4P and 5A-5P together as discussed above, the implant 10 can be used in any anatomical location. The implant 10 can be formed to correspond to a natural and/or desired size and shape of any anatomical location while the body is static (e.g., upright, bent over, supine, prone, or any position in which the body is "frozen" in time) or in motion (e.g., walking, running, jumping, or any other movement). For example, in certain embodiments, the implant 10 is formed to correspond to a desired and/or natural shape of the left or right cheek of the buttocks, or a portion thereof. As shown and described above, the implant 10 can be a truncated approximately ovoid implant bounded by convex upper and concave lower surfaces 10a, 10b, with other truncated shapes also being appreciated, such as, for example, ellipsoids, approximately ellipsoidal, substantially ellipsoidal, ovoids, substantially ovoidal spheres, approximately spherical, substantially spherical spheroids, approximately spheroidal, teardropoids, approximately teardropoidal, substantially teardropoidal, paraboloids, approximately paraboloidal, polygonoids, approximately polygonoidal, or substantially polygonoidal, among any other suitable shape having curved and/or angular surfaces, including shapes with parametric and/or non-parametric surfaces. In certain embodiments, the convex upper surface of the implant has a continuous curvature. For example, in certain embodiments, the convex upper surface can form a single unitary piece of the implant. The continuous curvature of the convex upper surface can define an apex with a smooth surface which forms the topmost point of the implant. The apex may or may not be centered with respect to convex upper surface (e.g., it can be centered or off-centered). In certain embodiments, the concave lower surface has a continuous curvature. For example, in certain embodiments, the concave lower surface can form a single unitary piece of the implant. The continuous curvature of the concave lower surface can define a depression into the body of the implant that substantially mirrors the shape of the convex upper surface. In other embodiments, the convex upper surface and concave lower surface can be angular such that it approximates a smooth surface, and in certain embodiments, the upper and lower surfaces can have angled portions in addition to curved portions. In certain embodiments the lower surface is concave to cup the underlying tissue for a better fit. Advantageously, the concavity of the lower surface can help reduce or eliminate the risk of mal-rotation and/or mal-translation events. For example, in certain embodiments, the concavity can be shaped to form a suction force against the underlying tissue upon implantation to prevent or reduce the occurrence of mal-rotation and/or mal-translation events. In certain embodiments, the surface of the concavity can be smooth or coarse. When the surface is coarse, the surface of the concavity can generate friction between the concave lower surface and the tissue so that it takes more force to mal-rotate and/or mal-translate the implant. In some embodiments, when the surface of the concavity is smooth, the concave surface can include one or more tissue hooks configured to extend into the tissue and prevent mal-translation and/or mal-rotation.

While in certain embodiments well-known geometric shapes and/or surfaces are used to form the implants shown and described herein, customized shapes and/or surfaces are appreciated as well and can be used in lieu of or in tandem therewith. In addition, in certain embodiments, such customized shapes can approximate well-known geometric shapes. For example, the implant 10 in FIGS. 4A-4P approximates a truncated ovoid. However, other approximations are also possible, such as, for example, ellipsoids, spheres, spheroids, teardropoids, paraboloids, or polygonoids, as well as truncations thereof.

The shapes and/or surfaces of the implant can be chosen, designed, and/or formed according to the body region in which the implant will be implanted, in addition to myriad other factors. For example, FIGS. 4A-4P show an implant 10 having a truncated approximately or substantially ovoid shape for the left or right buttock, and which can be formed in several ways. For example, in certain embodiments, the lower concave and upper convex surfaces 10b, 10a of the truncated approximately or substantially ovoid implant 10 can be formed by creating the inner and outer arc 23, 25 arrangement depicted in FIG. 4H in a computer-aided design (CAD) computer program. This arc section can then be pulled simultaneously in a first lengthwise direction and a second downward direction until its perimeter profile matches that of half of the profile 11 depicted in FIG. 4F and such that its inner and outer arc 25, 27 in the plane orthogonally centered with respect to the plane containing the inner and outer arc 23, 25 have the radii shown in FIG. 4K. This graphical extrusion can then be reflected across the plane containing the inner and outer arc 23, 25 to complete the truncated approximately ovoid implant 10. Of course, any suitable combination of arcs that intersect and terminate at two points is also appreciated, as is any suitable subsequent extrusion and reflection that ultimately form the implant.

Generally, in certain embodiments, the convex upper and concave lower surfaces of an implant can be formed from any two like shaped surfaces, such as, for example, ellipsoidal surfaces, approximately ellipsoidal surfaces, and/or substantially ellipsoidal surfaces, or ovoidal surfaces, approximately ovoidal surfaces, and/or substantially ovoidal surfaces, or spherical surfaces, approximately spherical surfaces, and/or substantially spherical surfaces, or spheroidal surfaces, approximately spheroidal surfaces, and/or substantially spherical surfaces, or teardropoidal surfaces, approximately teardropoidal surfaces, and/or substantially teardropoidal surfaces, or cylindrical surfaces, approximately cylindrical surfaces, and/or substantially cylindrical surfaces, or polygonal surfaces, approximately polygonal surfaces, and/or substantially polygonal surfaces, or paraboloidal surfaces, approximately paraboloidal surfaces, and/or substantially paraboloidal surfaces, among others, including shapes with parametric and/or non-parametric surfaces. In other embodiments, the convex upper and concave lower surfaces $10a$, $10b$ have different relative shapes or a combination of two or more shaped surfaces, with the upper convex surface forming a first surface and the lower concave surface forming a second surface. For example, in certain embodiments, the upper surface can be formed from an ellipsoidal surface, an approximately ellipsoidal, or a substantially ellipsoidal surface and the lower surface can be formed from any suitable shaped surface different from ellipsoidal, approximately ellipsoidal, or substantially ellipsoidal such as, for example, ovoidal, approximately ovoidal, substantially ovoidal, spherical, approximately spherical, substantially spherical, spheroidal, approximately spheroidal, substantially spheroidal, teardropoidal, approximately teardropoidal, substantially teardropoidal, cylindrical, approximately cylindrical, substantially cylindrical, polygonal, approximately polygonal, or substantially polygonal, among others, including shapes with parametric and/or non-parametric surfaces. In still other embodiments, the upper and lower surfaces $10a$, $10b$ can be any suitably shaped surface as discussed above.

However, in certain embodiments it is advantageous not to have the upper and/or lower surface of the implant be cylindrical shaped, such as cylindrical or approximately cylindrical (e.g., having a substantially constant height along at least a portion of the lower surface) because a cylindrical or approximately cylindrical lower surface will encourage the implant to translate along the cylindrical axis and also make it harder to rotate the implant back into an equilibrium position following a post-operative movement (e.g., because the edges of the lower surface are more likely to catch tissue and make rotation harder).

Further, in certain embodiments, it is advantageous to use shapes that are truncated ovoids, truncated approximate ovoids, substantially truncated ovoids, truncated ellipsoids, truncated approximate ellipsoids, or substantially truncated ellipsoids instead of truncated spheres, truncated approximate spheres, or substantially truncated spheres because, for similar sized three dimensional bodies, the former list conforms better to the buttock region and muscle insertion points than truncated spheres or truncated approximate spheres. For example, truncated spheres, truncated approximate spheres, or substantially truncated spheres typically have peaks that are too short (i.e., the peak of the convex upper surface of the implant is not high enough), and they typically aren't large enough to reach the back of the thigh. As a result, truncated spheres, truncated approximate spheres, or substantially truncated spheres typically have less desirable aesthetic properties upon implantation when compared to truncated ovoids, truncated approximate ovoids, substantially truncated ovoids, truncated ellipsoids, truncated approximate ellipsoids, or substantially truncated ellipsoids.

For example, with reference to FIGS. 5A-5P, the upper surface $10a$ can be formed from the surface of a first ellipsoid, the upper surface $10a$ being a truncated portion thereof, and the lower surface $10b$ can be formed from the surface of a second ellipsoid, the lower surface $10b$ being a truncated portion thereof, such that the upper and lower surfaces $10a$, $10b$ are formed from a truncated surface of the first and second ellipsoid, respectively. Thus, in certain embodiments, the implant 10 is formed from a single ellipsoid while its upper and lower surfaces $10a$, $10b$ are defined by the truncated surfaces of two ellipsoids.

Figure 6A:
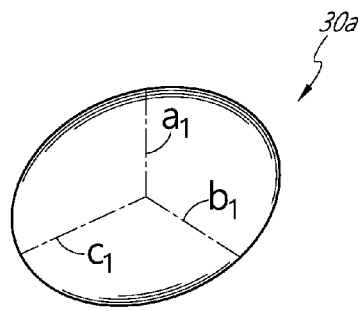
FIGS. 6A-6C show two ellipsoids and a combination thereof, the combination partly defining the truncated ellipsoid implant illustrated in FIGS. 5A-5P.
Figure 6B:
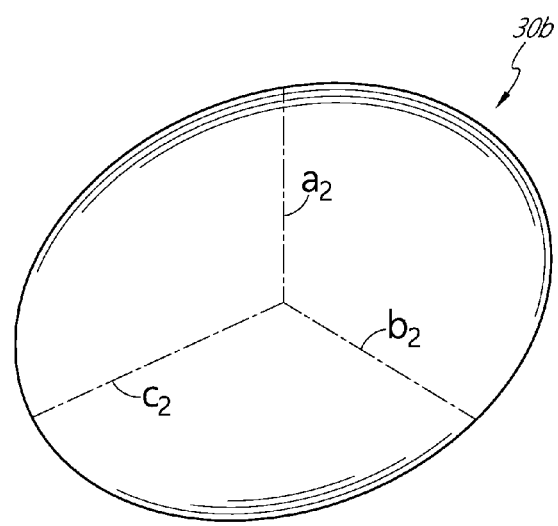
Figure 6C:
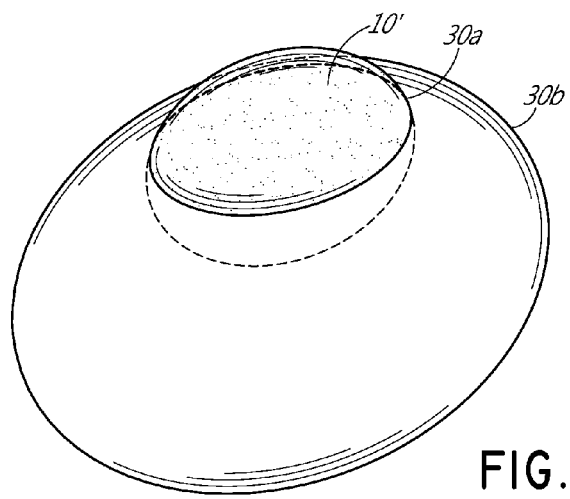

In certain embodiments, the implant 10' can be formed from one or more three dimensional bodies and/or surfaces. For example, FIGS. 6A and 6B illustrate two ellipsoids that are capable of forming the implant 10'. In particular, FIG. 6A illustrates a first ellipsoid $30a$ which forms the implant 10' and its upper surface $10a$, and FIG. 6B illustrates a second ellipsoid $30b$ which forms the lower surface $10b$ of the implant 10. In Cartesian coordinates, the first and second ellipsoid $30a$, $30b$ are defined by:

$$x^2/a^2+y^2/b_3+z^2/c^2=1,$$

where a, b, and c correspond to the semi-major and semi-minor axes of the three ellipses that re formed at the three axial cross-sections coincident with the XY-plane, XZ-plane, and YZ-plane, and where the points (a, 0, 0), (0, b, 0), and (0, 0, c) correspond to surface coordinates. For example, FIGS. 6A and 6B, show semi-major axes $c_1$, $c_2$ and semi-minor axes $b_1$, $b_2$ in the XY-plane, semi-major axes $b_1$, $b_2$ and semi-minor axes $a_1$, $a_2$ in the XZ-plane, and semi-major axes $c_1$, $c_2$ and semi-minor axes $a_1$, $a_2$ in the YZ-plane. FIG. 6C illustrates the implant 10' formed by the combination of the first and second ellipsoids $30a$, $30b$. In certain embodiments, $a_1$, $a_2$, $b_1$, $b_2$, $c_1$, and $c_2$ are chosen such that the implant has a convex upper surface and a concave lower surface as described above with reference to FIGS. 4A-4P and 5A-5P.

Further, in certain embodiments, the semi-major axis c and the semi-minor axis b of the first and/or second ellipsoid $30a$, $30b$ in the XY-plane correspond to the semi-major axis and semi-minor axis of the two dimensional projection of the perimeter of the implant in the XY-plane, depending on the size and extent of the truncation.

Figure 7A:
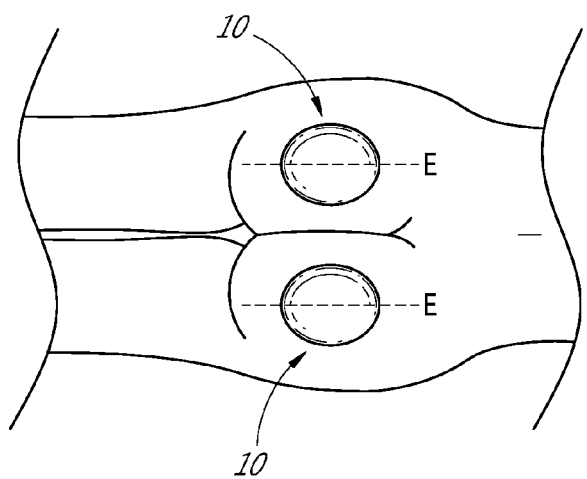
FIGS. 7A-7C sequentially illustrate the implant of FIGS. 4A-4P in an implanted equilibrium position, a shifted position, and a restored equilibrium position.
Figure 7B:
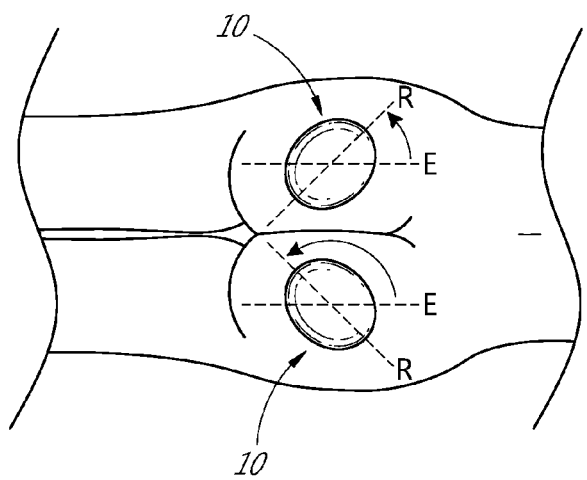
Figure 7C:
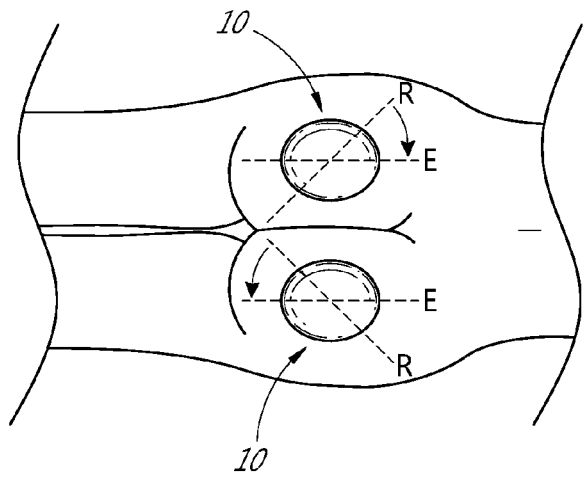

As discussed above, in certain embodiments, the size and shape of the implant 10 is formed so that it has one or more positions of stability upon implantation, such as for example two equilibrium positions. For example, FIGS. 7A-7C illustrate the implant 10 of FIGS. 4A-4P in three sequential positions (e.g., a first equilibrium position, a first non-equilibrium position, and a second equilibrium position), although any suitable implant is appreciated. In FIG. 7A, two implanted implants 10 are shown aligned with axes E in an equilibrium position. In FIG. 7B, the two implants have been rotated out of their equilibrium positions and are now aligned with axes R. FIG. 7C illustrates the implants 10 in FIG. 7B rotated back into an equilibrium position and again aligned with axes E.

Figure 11:
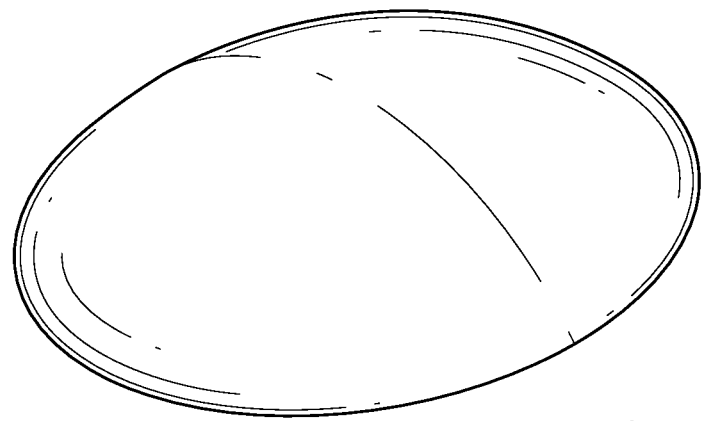
FIG. 11 is a top perspective view of the implant of FIGS. 4A-4P.
Figure 12:
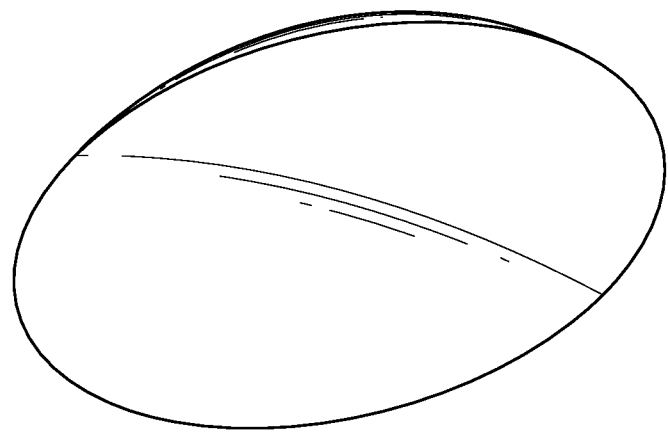
FIG. 12 is a bottom perspective view of the implant of FIGS. 4A-4P.
Figure 13:
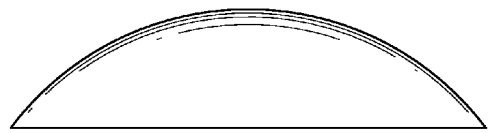
FIG. 13 is a front view of the implant of FIGS. 4A-4P.
Figure 14:
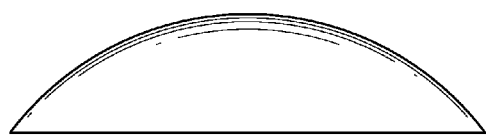
FIG. 14 is a rear view of the implant of FIGS. 4A-4P.
Figure 15:
FIG. 15 is a left side view of the implant of FIGS. 4A-4P.
Figure 16:
FIG. 16 is a right side view of the implant of FIGS. 4A-4P.
Figure 17:
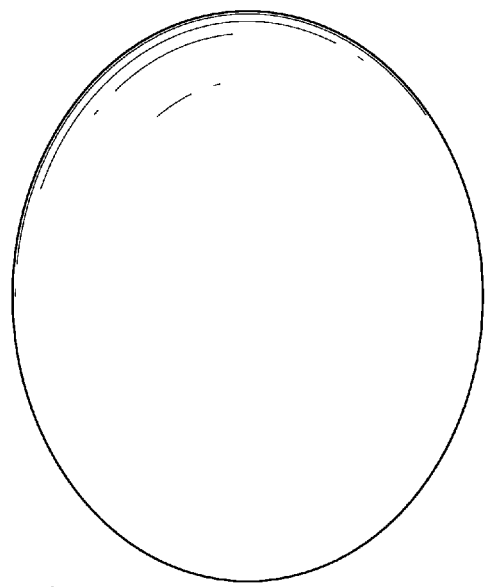
FIG. 17 is a top plan view of the implant of FIGS. 4A-4P.
Figure 18:
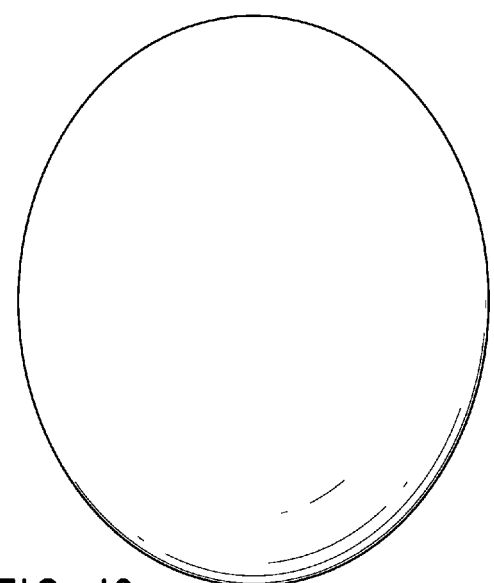
FIG. 18 is a bottom plan view of the implant of FIGS. 4A-4P.

FIGS. 11-18 illustrate additional views of the implant 10 depicted in FIGS. 4A-4P. For example, FIG. 11 illustrates a top perspective view of the implant of FIGS. 4A-4P, FIG. 12 illustrates a bottom perspective view of the implant of FIGS. 4A-4P, FIG. 13 illustrates a front view of the implant of FIGS. 4A-4P, FIG. 14 illustrates a rear view of the implant of FIGS. 4A-4P, FIG. 15 illustrates a left side view of the implant of FIGS. 4A-4P, FIG. 16 illustrates a right side view of the implant of FIGS. 4A-4P, FIG. 17 illustrates a top plan view of the implant of FIGS. 4A-4P, FIG. 18 illustrates a bottom plan view of the implant of FIGS. 4A-4P.

Depending on patient anatomy and patient preferences, the same sized oval implant might be used for both the left and right implant, but this is not required. For example, left and right implants of different sizes and different shapes can easily be combined and result in a balanced post-surgical aesthetic appearance. In yet other embodiments, an unrestrained symmetrical infinity shaped ovoid or approximately ovoid implant system is used to help solve the problem of post-operation implant movement. In these embodiments, the implant system is a type of hybrid between the restrained asymmetrical implant systems and the unrestrained implants described above. For example, these embodiments have symmetry about two axes, and although unrestrained, have left and right buttock implants that are nevertheless connected. Similar to the implants described above, infinity shaped ovoid or approximately ovoid implant systems can also act to mitigate and potentially eliminate the risk of mal-rotation and mal-translation events due to their large size and expansive anatomical presence. The size and shape of infinity shaped ovoid or approximately ovoid implant systems are designed to resist post-operative implant movement.

Figure 8C:
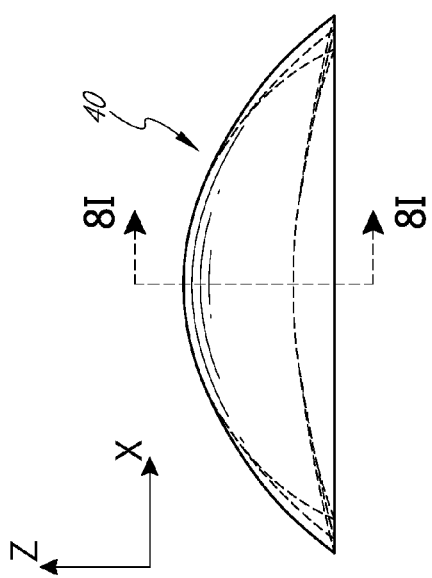
FIGS. 8A-8O are various views of an infinity shaped implant.
Figure 8D:
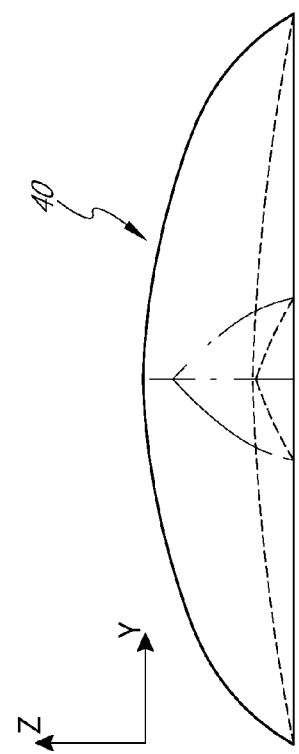
Figure 8F:
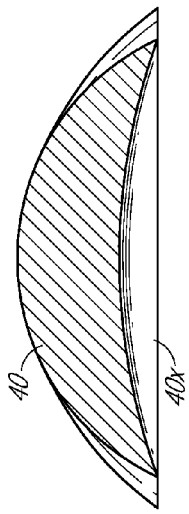
Figure 8G:
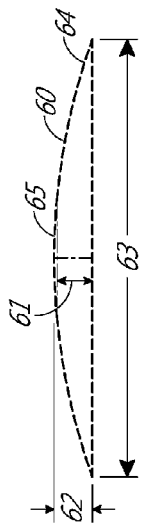
Figure 8H:
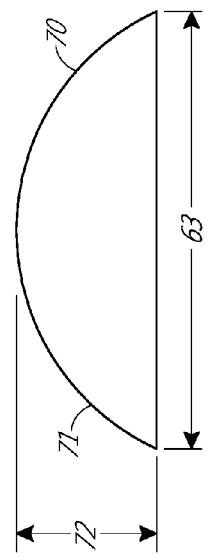
Figure 8E:
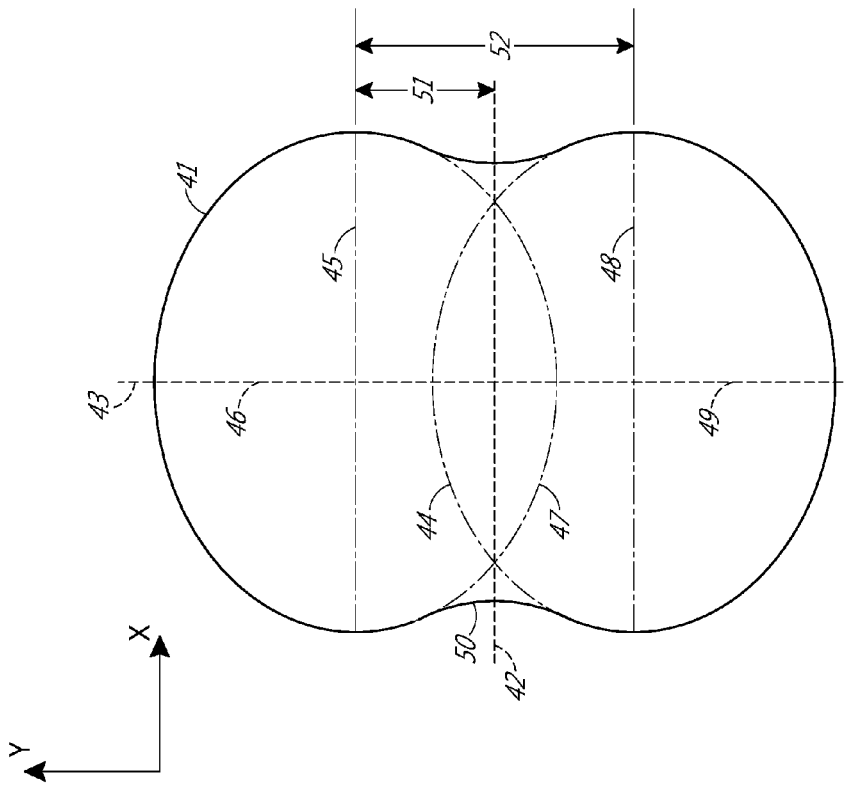
Figure 8I:
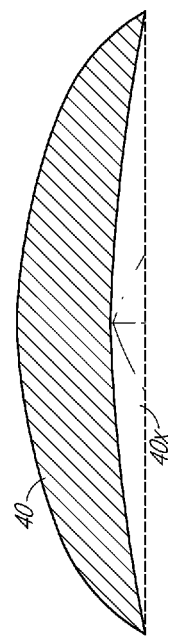
Figure 8J:
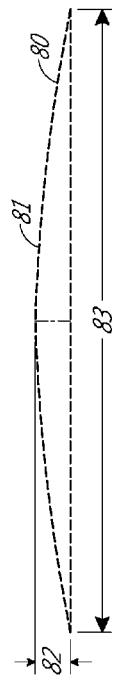
Figure 8K:
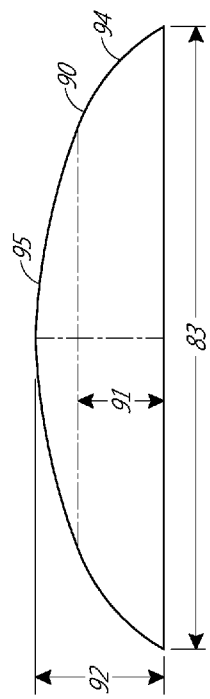
Figure 8L:
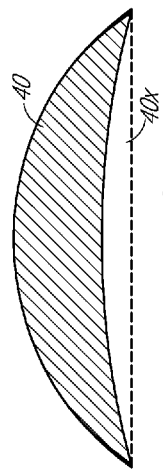
Figure 8M:
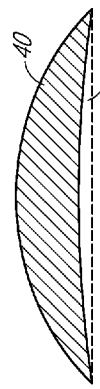
Figure 8N:
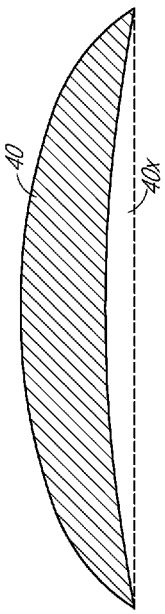
Figure 8O:
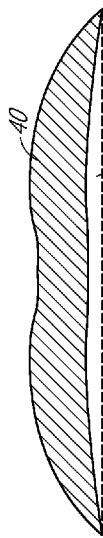

FIGS. 8A-8O illustrate various views of an exemplary infinity shaped implant 40 with a concave lower surface. For example, in certain embodiments, the infinity shaped implant 40 is a truncated ovoid or approximately ovoid implant with a concave lower surface Specifically, FIG. 8A illustrates a top view, FIG. 8B illustrates a perspective view, and FIGS. 8C and 8D illustrate side views of a symmetrical infinity shaped ovoid or approximately ovoid implant system 40. Together, FIGS. 8A-8D show that the symmetrical infinity shaped implant system 40 has two axes of symmetry about axes X and Y. FIG. 8E illustrates the outer profile 41 of the infinity shaped implant system 40. The outer profile 41 is formed by joining two symmetric ovals together. In certain embodiments, outer profile 41 comprises two separate oval profiles 44 and 47 joined together at a horizontal center line 42 by a connecting arc 50 on each side. The oval profiles 44 and 45 have the symmetry described above with reference to FIG. 4F. In certain embodiments, the horizontal center line 42 is parallel to major axes 45 and 48 of oval profiles 44 and 47, respectively, and defines an inner waist of outer profile 41. In certain embodiments, the major axes 45 and 48 are a constant separating distance 52 apart and a distance 51 from the horizontal center line. Moreover, the minor axes 46 and 49 of oval profiles 44 and 47, respectively, are coincident with one another near the horizontal center line 42. In certain embodiments, the minor axes 46 and 49 together define a vertical center line 43 that runs the length of outer implant profile 41 as shown in FIG. 8E. As shown, the infinity ovoid implant system is symmetric about the horizontal center line 42 and the vertical center line 43. In certain embodiments, the major axes 45 and 48, minor axes 46 and 49, distance 51, and separating distance 52 have lengths of approximately 12 cm, 10 cm, 3 cm, and 7 cm, respectively, and the connecting arc 50 has a radius of approximately 4 centimeters. Other suitable lengths and radii are appreciated. For example, the major axes 45 and 48, minor axes 46 and 49, distance 51, and separating distance 52 may range from approximately 7-16 cm, 8-12 cm, 2-6 cm, and 5-9 cm, respectively, and the connecting arc 51 may range from 2-6 cm. In addition, the ratio of the inner waist, or horizontal center line 42, to the major axes 45 and 48 is about 0.88 in FIG. 8E. However, other ratios are appreciated. For example, the ratio of the inner waist to the major axes may range, for example, from between about 0.75 to about 0.97, between about 0.80 and about 0.95, between about 0.85 and about 0.90, or about 0.75, 0.76, 0.77, 0.78, 0.79, 0.80, 0.81, 0.82, 0.83, 0.84, 0.85, 0.86, 0.87, 0.88, 0.89, 0.90, 0.91, 0.92, 0.93, 0.94, 0.95, 0.96, or 0.97.

FIGS. 8C and 8D further illustrate side views of the infinity shaped implant system 40 shown in FIGS. 8A and 8B. In particular, FIG. 8C is a side view in the XZ-plane and FIG. 8D is a side view in the YZ-plane. As shown, the implant is symmetrical across the Z axis in both figures.

FIGS. 8F and 8I illustrate center side view cross-sections in the XZ- and YZ-planes at line 8F-8F in FIG. 8A and at line 8I-8I in FIG. 8C, respectively, of a concave infinity shaped implant. In particular, FIGS. 8F and 8I illustrate cross sections of the implant 40 and a concavity 40x. Similarly, FIG. 8L illustrates the implant in the XZ-plane at line 8L-8L in FIG. 8A, FIG. 8M illustrates the implant in the XZ-plane at line 8M-8M in FIG. 8A, FIG. 8N illustrates the implant in the XZ-plane at line 8N-8N in FIG. 8A, and FIG. 8O illustrates the implant in the XZ-plane at line 8O-8O in FIG. 8A. As shown in these figures, the arc lengths can decrease as the cross-sections are taken closer to the peripheral edge of the implant. For example, in certain embodiments, the shapes of the arcs approach one another until they merge into a single horizontal line at the peripheral edge of the implant. In certain embodiments, the distance between the upper and lower surfaces can decrease to zero toward the peripheral edge of the implant. In certain embodiments, the angle between the upper and lower surfaces can decrease to zero toward the peripheral edge of the implant. As shown in FIGS. 8A-8O, the slope of the surface of the implant varies.

In particular, FIG. 8G illustrates a narrow center concavity profile 60 in the XZ-plane and FIG. 8H illustrates the corresponding narrow center implant profile 70 in the XZ-plane. The exemplary cross sections in FIGS. 8G and 8H are at the narrowest point of the infinity ovoid implant system along the horizontal center line 42 shown in FIG. 8E. In certain embodiments, the concavity profile 60 is defined by horizontal centerline length 63, narrow lower concavity radius 64, and narrow upper concavity radius 65 as shown in FIG. 8G. In certain embodiments, the vertical distance between the highest point of the narrow lower concavity radius 64 and the horizontal centerline length 63 is the narrow lower concavity height 61 and the vertical distance between the highest point of the narrow upper concavity radius 65 and the horizontal centerline length 63 is the narrow upper concavity height 62. In certain embodiments, the horizontal centerline length 63, narrow lower concavity radius 64, narrow upper concavity radius 65, narrow lower concavity height 61, and narrow upper concavity height 62 have lengths or radii of approximately 11 cm, 16 cm, 15 cm, 0.9 cm, and 1 cm, respectively. Other suitable lengths and radii are appreciated. For example, the horizontal centerline length 63, narrow lower concavity radius 64, narrow upper concavity radius 65, narrow lower concavity height 61, and narrow upper concavity height 62 can have lengths and radii that respectively range from approximately 8-14 cm, 12-20 cm, 0.5-1.5 cm, and 0.5-1.5 cm.

In certain embodiments, the narrow center implant profile 70 is defined by horizontal centerline length 63 and narrow implant radius 71 as shown in FIG. 8H. In certain embodiments, the vertical distance between the highest point of the narrow implant radius 71 and the horizontal centerline length 63 is the narrow implant height 72. In certain embodiments, the horizontal centerline length 63, narrow implant radius 71, and narrow implant height 72 have lengths and a radius of approximately 11 cm, 6 cm, and 3.5 cm, respectively. Other suitable lengths and radii are appreciated. For example, the horizontal centerline length 63, narrow implant radius 71, and narrow implant height 72 can have lengths and radii that respectively range from approximately 8-14 cm, 3.5-9 cm, and 2.5-6 cm.

Similarly, FIG. 8J illustrates a wide center concavity profile 80 in the YZ-plane and FIG. 8K illustrates the corresponding wide center implant profile 90 in the YZ-plane. The exemplary cross sections in FIGS. 8J and 8K are at the widest point of the infinity ovoid implant system along the union of minor axes 46 and 49 shown in FIG. 8E. In certain embodiments, the wide center concavity profile 80 is defined by distance 83, which is the line created via some combination of both minor axes 46 and 49 shown in FIG. 5F, and the wide concavity radius 81. In certain embodiments, the vertical distance between distance 83 and the highest point of the wide concavity radius 81 is the wide concavity height 82. In certain embodiments, distance 83, wide concavity radius 81, and wide concavity height 82 have lengths and a radius of approximately 17 cm, 52 cm, and 1 cm, respectively. Other suitable lengths and radii are appreciated. For example, distance 83, wide concavity radius 81, and wide concavity height 82 may have lengths and radii that respectively range from approximately 12-22 cm, 45-57 cm, and 0.5-1.5 cm.

As shown in FIG. 8K, in certain embodiments, the wide center implant profile 90 is defined by is defined by distance 83, which is the line created via some combination of both minor axes 46 and 49 shown in FIG. 8E, and wide lower implant radius 94, and wide upper implant radius 95. In certain embodiments, the vertical distance between the highest point of wide lower implant radius 94 and distance 83 is the wide lower implant height 91 and the vertical distance between the highest point of wide upper implant radius 95 and distance 83 is the wide upper implant height 92. In certain embodiments, distance 83, wide lower implant radius 94, wide upper implant radius 95, wide lower implant height 91, and wide upper implant height 92 have lengths or radii of approximately 17 cm, 5 cm, 17.5 cm, 2 cm, and 3.5 cm, respectively. Other suitable lengths and radii are appreciated. For example, distance 83, wide lower implant radius 94, wide upper implant radius 95, wide lower implant height 91, and wide upper implant height 92 may have lengths and radii that respectively range from approximately 12-22 cm, 3-8 cm, 14-21 cm, 1.5-3.5 cm, and 2-5 cm.

The implants and implant systems shown and described herein can be manufactured from, for example, silicone or silicone reinforced with a material such as Dacron, polystyrene, polypropylene, propylene, prolene, PTFE, ePTFE, composite materials and other natural, biological and synthetic materials. The silicone rubber material durometer, or softness, at the implant surfaces can range from "A-scale" 50-20, such as about 50, 45, 40, 35, 30, 25, 20, or ranges including one or more of the foregoing values, and can range from "00-scale" 50-"000-scale" 10 at the implant center, such that the implant shape is stable. In certain embodiments, the implants and implant systems described herein are formed by injection molding, or any other suitable process. In some embodiments, the implant, e.g., the outer shell of the implant is not made of a plastic material. In some embodiments, the implant has a flexible body that is not rigid to mimic natural body contours, including the buttocks, and is configured such that the surrounding native tissue can move vis-à-vis the implant. The implant can have a smooth or textured surface in some embodiments.

Further, the implants and implant systems can include a body that includes a shell having one unitary layer, or a plurality of layers, such as 2, 3, 4, or more layers and filled or configured to be substantially filled with a filler such as a viscous flowable material, and/or a foam. The viscous material can be selected for a combination of non-toxicity as well as to provide structural support to the surrounding tissue while maintaining a natural feel. For example, the viscous material can include saline, water, silicone, silicone gel, a triglyceride oil, a block co-polymer, or other materials. In some embodiments, the implant can be configured to be filled with any desired volume, such as for example between about 200 cc and about 1000 cc or between about 200 cc and about 800 cc.

In certain embodiments, a method includes implanting any of the embodiments shown and/or described herein into a human body, the method comprising preparing a surgical site, forming a cavity for the implant, and implanting the embodiment in the surgically created cavity. Any of the embodiments shown and/or described herein can be utilized, for example, for breast or buttock augmentation and/or reconstruction. In some embodiments, the implant is configured to be a permanent implantable prosthesis for insertion in the body for at least about 1, 2, 3, 4, 5, 6, 7, 8, 9, 10, 15, 20, 25 years, and not as a temporary implant, such as after reconstructions for example.

OTHER EMBODIMENTS

The following described embodiments are other embodiments contemplated by this disclosure:

1. An implantable gluteoplasty system comprising:
   a first gluteal implant and a second gluteal implant;
   at least one connector configured to connect the first gluteal implant and the second gluteal implant, the at least one connector configured to restrain the plurality of implants from at least one of mal-rotation and mal-translation; and
   a first fastener configured to secure the at least one connector to the first gluteal implant and a second fastener configured to secure the at least one connector to the second gluteal implant.

2. The implantable gluteoplasty system of embodiment 1, wherein the first and second gluteal implants each comprise a feature configured to receive the at least one connector and at least one of the fasteners.

3. The implantable gluteoplasty system of embodiment 2, wherein the feature comprises a surface depression.

4. The implantable gluteoplasty system of embodiment 3, wherein the surface depression comprises one or more restraining grooves configured to receive a portion of the at least one connector and comprises one or more apertures configured to receive one or more of the fasteners and a portion of the at least one connector, the one or more apertures further configured such one or more the apertures are proximate to each terminal end of the one or more restraining grooves.

5. The implantable gluteoplasty system of embodiment 4, wherein the one or more apertures each comprise a surface cavity and an interior cavity, the surface cavity configured to receive a portion of the at least one connector and a portion of at least one of the fasteners and the interior cavity configured to receive a portion of at least one of the fasteners.

6. The implantable gluteoplasty system of embodiment 1, wherein the at least one connector further comprises a central elongate member having a proximal end and a distal end, wherein the proximal end and the distal end are proximate one or more implant attachment features.

7. The implantable gluteoplasty system of embodiment 6, wherein the central elongate member has a fixed length.

8. The implantable gluteoplasty system of embodiment 6, wherein the central elongate member has an adjustable length.

9. The implantable gluteoplasty system of embodiment 6, wherein the one or more implant attachment features comprise one or more rings.

10. The implantable gluteoplasty system of embodiment 9, wherein the one or more rings are detachable.

11. The implantable gluteoplasty system of embodiment 1, wherein the first gluteal implant is configured for implantation in a left buttock and the second gluteal implant is configured for implantation in a right buttock.

12. The implantable gluteoplasty system of embodiment 1, wherein the first gluteal implant and the second gluteal implant are one of ovoid shaped and ellipsoid shaped.

13. The implantable gluteoplasty system of embodiment 1, wherein the first gluteal implant and the second gluteal implant are one of approximately ovoid shaped and approximately ellipsoid shaped.

14. The implantable gluteoplasty system of embodiment 1, wherein the at least one connector is configured to exert a tension force on the first gluteal implant and the second gluteal implant.

15. An implantable gluteoplasty system comprising:
a gluteal implant having an infinity shape.

16. The implantable gluteoplasty system of embodiment 15, wherein the infinity shape comprises two symmetrical implants joined together.

17. The implantable gluteoplasty system of embodiment 16, wherein the two symmetrical implants are joined together by a connecting arc defining an inner waist of the implant.

18. The implantable gluteoplasty system of embodiment 16, wherein the two symmetrical implants comprise a first and second gluteal implant having symmetrical ovoid shapes.

19. The implantable gluteoplasty system of embodiment 16, wherein the two symmetrical implants comprise a first and second gluteal implant having symmetrical approximately ovoid shapes.

20. The implantable gluteoplasty system of embodiment 16, wherein the two symmetrical implants comprise a first and second gluteal implant having symmetrical ellipsoid shapes.

21. The implantable gluteoplasty system of embodiment 16, wherein the two symmetrical implants comprise a first and second gluteal implant having symmetrical approximately ellipsoid shapes.

22. The implantable gluteoplasty system of embodiment 16, wherein the infinity shaped gluteal implant is concave.

23. An implantable gluteoplasty system comprising:
a first gluteal implant and a second gluteal implant, wherein the first and second gluteal implants are each symmetrical across two coordinate planes.

24. The implantable gluteoplasty system of embodiment 23, wherein the first and second gluteal implants are symmetrical ovoid implants.

25. The implantable gluteoplasty system of embodiment 23, wherein the first and second gluteal implants are symmetrical ellipsoid implants.

26. The implantable gluteoplasty system of embodiment 23, wherein the first and second gluteal implants are concave.

27. The implantable gluteoplasty system of embodiment 23, wherein the first and second gluteal implants are not "tear-drop" shaped.

Any apparatus and method described in this application can include any combination of the preceding features described in this and other paragraphs, among other features and combinations described herein, including features and combinations described in subsequent paragraphs, and including any features and combinations described in any application incorporated by reference herein.

Various other modifications, adaptations, and alternative designs are of course possible in light of the above teachings. For example, while generally described in the context of gluteal implants, embodiments could also be applied to other anatomical locations such as breast implants for example. Therefore, it should be understood at this time that within the scope of any appended claims the invention may be practiced otherwise than as specifically described herein. It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A gluteal implant comprising:
a body comprising:
a convex upper surface;
a concave lower surface; and
a peripheral edge, the edge defined by the intersection between the convex upper surface and the concave lower surface,
wherein the body is symmetrical across two orthogonal reference planes and comprises one of a truncated ovoid shape, a truncated approximate ovoid shape, a truncated ellipsoid shape, and a truncated approximate ellipsoid shape,
wherein the convex upper surface comprises one of a portion of a first surface selected from the group consisting of: an ovoid surface, an approximate ovoid surface, an ellipsoid surface, and an approximate ellipsoid surface, said first surface having a first semi-major axis and a first radius of curvature and a first semi-minor axis and a second radius of curvature,
wherein the concave lower surface comprises one of a portion of a second surface selected from the group consisting of: an ovoid surface, an approximate ovoid surface, an ellipsoid surface, and an approximate ellipsoid surface, said second surface having a second semi-major axis and a third radius of curvature and a second semi-minor axis and a fourth radius of curvature,
wherein the convex upper surface forms a peak of the implant,
wherein the concave lower surface forms a peak of a concavity,
wherein the edge forms a bottommost point of the implant,
wherein the edge outlines an oval or ellipse when viewed from above,
wherein a ratio between the first radius of curvature and the second radius of curvature is in a range from about 0.3 to about 3.0,
wherein a ratio between the third radius of curvature and the fourth radius of curvature is in a range from about 0.3 to about 1.7,
wherein a ratio between the first radius of curvature and the third radius of curvature is in a range from about 1.1 to about 3.0,
wherein a ratio between the second radius of curvature and the fourth radius of curvature is in a range from about 1.5 to about 6.0,
wherein the shape of the body is configured to have rotational symmetry that conceals the effects of post-operative movement,
wherein the shape of the body is configured to facilitate movement toward an equilibrium position following post-operative movement away from an equilibrium position, wherein post-operative movement includes mal-translation or mal-rotation,
wherein the body comprises a unitary piece of material, and
wherein the concave upper surface and concave lower surface are smooth surfaces.

2. The gluteal implant of claim 1, wherein the shape of the body is configured to resist post-operative movement away from an equilibrium position, wherein post-operative movement includes mal-translation or mal-rotation.

3. The gluteal implant of claim 1, wherein the shape of the body is configured to facilitate movement toward an equilibrium position following post-operative movement away from an equilibrium position, wherein post-operative movement includes mal-translation or mal-rotation.

4. The gluteal implant of claim 1, wherein the body comprises a truncated ellipsoid shape, wherein the convex upper surface comprises a portion of an ellipsoid surface, and wherein the concave lower surface comprises a portion of an ellipsoid surface.

5. The gluteal implant of claim 1, wherein the body comprises a truncated approximate ovoid shape, wherein the convex upper surface comprises a portion of an approximate ovoid surface, and wherein the concave lower surface comprises a portion of an approximate ovoid surface.

6. The gluteal implant of claim 1, wherein the convex upper surface has a radius of curvature of about 9 cm when viewed in cross section in a first plane and a radius of curvature of about 12 cm when viewed in cross section in a second plane orthogonal to the first plane, and wherein the concave lower surface has a radius of curvature of about 25 cm when viewed in cross section in the first plane and a radius of curvature of about 18 cm when viewed in cross section in the second plane.

7. The gluteal implant of claim 1, wherein the convex upper surface has a radius of curvature in the range of from about 5 cm to about 15 cm when viewed in cross section in a first plane and a radius of curvature in the range of from about 7 cm to about 18 cm when viewed in cross section in a second plane orthogonal to the first plane, and wherein the concave lower surface has a radius of curvature in the range of from about 18 cm to about 32 cm when viewed in cross section in the first plane and a radius of curvature in the range of from about 11 cm to about 25 cm when viewed in cross section in the second plane.

8. The gluteal implant of claim 1, wherein the angle of intersection varies along the edge of the implant.

9. The gluteal implant of claim 1, wherein the body is not "tear-drop" shaped.

10. The gluteal implant of claim 1, wherein the body is made of silicone.

11. A gluteal implant system comprising:
a first gluteal implant and a second gluteal implant, the first and second gluteal implants having convex curved superior first and concave second inferior surfaces, the curvature of the first surface being different from the curvature of the second surface,
wherein the first and second gluteal implants have reflective symmetry about exactly two orthogonal planes,
wherein the first and second gluteal implants comprise a body having one of a truncated ovoid shape, a truncated approximate ovoid shape, a truncated ellipsoid shape, and a truncated approximate ellipsoid shape,
wherein the shape of the body of the first and second gluteal implants is configured to have rotational symmetry that conceals the effects of post-operative movement,
wherein the shape of the body of the first and second gluteal implants is configured to resist a post-operative movement away from an equilibrium position and to facilitate movement toward an equilibrium position following a post-operative movement away from an equilibrium position, wherein post-operative movement includes mal-translation or mal-rotation of the body, and wherein the body of each of the first and second gluteal implants comprises a unitary piece of material.

12. The gluteal implant system of claim 11, wherein the body of the first and second gluteal implants comprises a truncated approximate ovoid shape.

13. The gluteal implant system of claim 11, wherein the body of the first and second gluteal implants comprises a truncated ellipsoid shape.

14. The gluteal implant system of claim 11, wherein the first surface is convex and the second surface is concave.

15. The gluteal implant system of claim 11, wherein the first and second gluteal implants are not "tear-drop" shaped.

16. The gluteal implant system of claim 11, wherein the shape of the body of the first and second gluteal implants is configured to resist a post-operative movement away from an equilibrium position and to facilitate movement toward an equilibrium position following a post-operative movement away from an equilibrium position, wherein post-operative movement includes mal-translation or mal-rotation of the body.

17. A gluteal implant comprising:
a body comprising:
a convex upper surface;
a concave lower surface; and
a peripheral edge, the edge defined by the intersection between the convex upper surface and the concave lower surface,
wherein the body is symmetrical across two orthogonal reference planes,
wherein the convex upper surface comprises one of a portion of a first surface selected from the group consisting of: an ovoid surface, an approximate ovoid surface, an ellipsoid surface, and an approximate ellipsoid surface, said first surface having a first semi-major axis and a first radius of curvature and a first semi-minor axis and a second radius of curvature,
wherein the concave lower surface comprises one of a portion of a second surface selected from the group consisting of: an ovoid surface, an approximate ovoid surface, an ellipsoid surface, and an approximate ellipsoid surface, said second surface having a second semi-major axis and a third radius of curvature and a second semi-minor axis and a fourth radius of curvature,
wherein the first radius of curvature differs from the third radius of curvature, wherein the difference is between about 2.22 cm and about 2.62 cm,
wherein the second radius of curvature differs from the fourth radius of curvature, wherein the difference is between about 2.72 cm and about 3.12 cm,
wherein the convex upper surface and the concave lower surface intersect at an angle ranging from about 15 degrees to about 40 degrees,
wherein the convex upper surface forms a peak of the implant,
wherein the concave lower surface forms a peak of a concavity,
wherein the edge forms a bottommost point of the implant,
wherein the edge outlines an oval or ellipse when viewed from above,
wherein the shape of the body is configured to have rotational symmetry that conceals the effects of post-operative movement,
wherein the shape of the body is configured to facilitate movement toward an equilibrium position following post-operative movement away from an equilibrium position, wherein post-operative movement includes mal-translation or mal-rotation,
wherein the body comprises a unitary piece of material, and
wherein the concave upper surface and concave lower surface are smooth surfaces.

18. A gluteal implant comprising:
a convex curved superior first and concave second inferior surfaces, the curvature of the first surface being different from the curvature of the second surface,
wherein the gluteal implant has reflective symmetry about exactly two orthogonal planes,
wherein the gluteal implant comprises a body having one of a truncated ovoid shape, a truncated approximate ovoid shape, a truncated ellipsoid shape, and a truncated approximate ellipsoid shape,
wherein the shape of the body of the gluteal implant is configured to have rotational symmetry that conceals the effects of post-operative movement,
wherein the shape of the body of the gluteal implant is configured to resist a post-operative movement away from an equilibrium position and to facilitate movement toward an equilibrium position following a post-operative movement away from an equilibrium position, wherein post-operative movement includes mal-translation or mal-rotation of the body, and
wherein the body of the gluteal implant comprises a unitary piece of material.

19. The gluteal implant of claim 18, wherein the gluteal implant comprises a truncated approximate ovoid shape.

20. The gluteal implant of claim 18, wherein the body of the gluteal implant comprises a truncated ellipsoid shape.

21. The gluteal implant of claim 18, wherein the gluteal implant is not "tear-drop" shaped.

* * * * *